(12) United States Patent
Tajima

(10) Patent No.: US 10,638,992 B2
(45) Date of Patent: May 5, 2020

(54) IMAGE PROCESSING APPARATUS, RADIOGRAPHY SYSTEM, IMAGE PROCESSING METHOD, AND IMAGE PROCESSING PROGRAM

(71) Applicant: FUJIFILM CORPORATION, Minato-ku, Tokyo (JP)

(72) Inventor: Takashi Tajima, Kanagawa (JP)

(73) Assignee: FUJIFILM CORPORATION, Tokyo (JP)

(*) Notice: Subject to any disclaimer, the term of this patent is extended or adjusted under 35 U.S.C. 154(b) by 134 days.

(21) Appl. No.: 15/974,721

(22) Filed: May 9, 2018

(65) Prior Publication Data

US 2018/0333119 A1  Nov. 22, 2018

(30) Foreign Application Priority Data

May 18, 2017 (JP) .................................. 2017-099106

(51) Int. Cl.
*A61B 6/00* (2006.01)
*G06T 7/11* (2017.01)
(Continued)

(52) U.S. Cl.
CPC ............. *A61B 6/482* (2013.01); *A61B 6/4266* (2013.01); *A61B 6/505* (2013.01); *A61B 6/5217* (2013.01);
(Continued)

(58) Field of Classification Search
CPC ....... A61B 6/482; A61B 6/505; A61B 6/5217; A61B 6/461; A61B 6/54; G06T 5/50;
(Continued)

(56) References Cited

U.S. PATENT DOCUMENTS

| 2010/0111395 A1* | 5/2010 | Tamakoshi | ............. | A61B 6/469 |
| | | | | 382/132 |
| 2016/0035451 A1* | 2/2016 | Tsuji | .................... | A61B 6/4266 |
| | | | | 378/62 |
| 2017/0055930 A1* | 3/2017 | Hagiwara | ................ | G06T 5/20 |

FOREIGN PATENT DOCUMENTS

JP     2011-56257 A     3/2011

OTHER PUBLICATIONS

Fujita et al., Effectiveness of the single-shot dual-energy subtraction technique for portal images, Journal of Applied Clinical Medical Physics, vol. 12, No. 4, Fall 2011, pp. 24-33 (Year: 2011).*

* cited by examiner

*Primary Examiner* — Said M Elnoubi
(74) *Attorney, Agent, or Firm* — Solaris Intellectual Property Group, PLLC

(57) ABSTRACT

A control unit of a console acquires first radiographic image data and second radiographic image data and determines whether a reference line which satisfies a predetermined accuracy for defining a bone mass is capable of being derived, on the basis of a pixel value of an initial soft region of a DXA profile indicating a correspondence relationship between a pixel position and the pixel value in a derivation region including a soft region and a bone region in a DXA image which is a difference image between a first radiographic image and a second radiographic image and is used to derive at least one of bone density or bone mineral content. In a case in which it is determined that the reference line is capable of being derived, the control unit derives the reference line on the basis of the pixel value of the initial soft region.

18 Claims, 18 Drawing Sheets

(51) Int. Cl.
*G06T 5/50* (2006.01)
*G06T 7/00* (2017.01)

(52) U.S. Cl.
CPC .............. *G06T 5/50* (2013.01); *G06T 7/0016* (2013.01); *G06T 7/11* (2017.01); *A61B 6/461* (2013.01); *A61B 6/54* (2013.01); *G06T 2207/10116* (2013.01); *G06T 2207/20224* (2013.01); *G06T 2207/30008* (2013.01); *G06T 2207/30024* (2013.01)

(58) Field of Classification Search
CPC ................ G06T 7/0012; G06T 7/0016; G06T 2207/10116; G06T 2207/30008; G06T 2207/20224; G06T 2207/30024
See application file for complete search history.

IMAGE PROCESSING APPARATUS, RADIOGRAPHY SYSTEM, IMAGE PROCESSING METHOD, AND IMAGE PROCESSING PROGRAM

CROSS-REFERENCE TO RELATED APPLICATION

This application claims priority under 35 USC 119 from Japanese Patent Application No. 2017-099106 filed May 18, 2017, the disclosure of which is incorporated by reference herein.

BACKGROUND

Technical Field

The present disclosure relates to an image processing apparatus, a radiography system, an image processing method, and an image processing program.

Related Art

In recent years, a technique has been known which derives at least one of the bone density and bone mineral content of a subject on the basis of the detection results of each radiation detector in a radiography apparatus including two radiation detectors that are stacked in a radiation emission direction and are irradiated with radiations having different energy levels (see JP2011-56257A). In the radiography apparatus, one radiation detector that is provided on the incident side of the radiation mainly absorbs a low-energy component of the radiation and generates image data of a radiographic image and the other radiation detector mainly absorbs a high-energy component of the radiation and generates image data of a radiographic image.

SUMMARY

In addition, a DXA profile which indicates a correspondence relationship between a pixel position and a pixel value and is derived using image data (for example, dual-energy X-ray absorptiometry (DXA) image data) generated on the basis of image data of two radiographic images generated by irradiation with (absorption of) radiations having different energy levels is used to derive bone density and bone mineral content.

However, in a case in which bone density and bone mineral content are derived using the DXA profile, the accuracy of derivation is likely to be reduced according to, for example, the state of the radiographic image.

The present disclosure has been made in view of the above-mentioned problems and an object of the present disclosure is to provide an image processing apparatus, a radiography system, an image processing method, and an image processing program that can improve the accuracy of derivation of at least one of bone density or bone mineral content.

In order to achieve the object, the present disclosure provides an image processing apparatus comprising: an acquisition unit that acquires a first radiographic image generated by a first radiation detector irradiated with radiation with a first energy level and a second radiographic image generated by a second radiation detector irradiated with radiation with a second energy level different from the first energy level from a radiography apparatus including the first and second radiation detectors in which a plurality of pixels, each of which includes a conversion element that generates a larger amount of charge as it is irradiated with a larger amount of radiation, are arranged and which are arranged in a direction in which the radiation is emitted; and a derivation unit that derives a reference line which satisfies a predetermined accuracy for defining a bone mass, on the basis of a pixel value of a predetermined region corresponding to a soft tissue in a profile indicating a correspondence relationship between a pixel position and the pixel value in a derivation region including a region corresponding to the soft tissue and a region corresponding to a bone tissue in a difference image for derivation which is a difference image between the first radiographic image and the second radiographic image and is used to derive at least one of bone density or bone mineral content.

In order to achieve the object, the present disclosure provides an image processing apparatus comprising: an acquisition unit that acquires a first radiographic image generated by a single radiation detector irradiated with radiation with a first energy level and a second radiographic image generated by the radiation detector irradiated with radiation with a second energy level different from the first energy level from a radiography apparatus including the radiation detector in which a plurality of pixels, each of which includes a conversion element that generates a larger amount of charge as it is irradiated with a larger amount of radiation, are arranged; and a derivation unit that derives a reference line which satisfies a predetermined accuracy for defining a bone mass, on the basis of a pixel value of a predetermined region corresponding to a soft tissue in a profile indicating a correspondence relationship between a pixel position and the pixel value in a derivation region including a region corresponding to the soft tissue and a region corresponding to a bone tissue in a difference image for derivation which is a difference image between the first radiographic image and the second radiographic image and is used to derive at least one of bone density or bone mineral content.

In the image processing apparatus according to the present disclosure, the derivation unit may comprise a determination unit that determines whether the reference line satisfying the predetermined accuracy is capable of being derived. In a case in which the determination unit determines that the reference line is capable of being derived, the derivation unit may derive the reference line.

In the image processing apparatus according to the present disclosure, in a case in which the determination unit determines that the reference line is not capable of being derived, the derivation unit may specify a region corresponding to the soft tissue and derive the reference line on the basis of a pixel value of the specified region corresponding to the soft tissue.

In the image processing apparatus according to the present disclosure, the determination unit may determine whether the reference line satisfying the predetermined accuracy is capable of being derived, on the basis of a variation in the pixel value of the region corresponding to the soft tissue in the profile.

In the image processing apparatus according to the present disclosure, in a case in which the determination unit determines that the reference line satisfying the predetermined accuracy is not capable of being derived, the derivation unit may derive the reference line on the basis of a pixel value of a region corresponding to the soft tissue which is wider than the predetermined region corresponding to the soft tissue.

In the image processing apparatus according to the present disclosure, in a case in which the profile includes a gas region caused by gas generated in a body of a subject from which at least one of the bone density or the bone mineral content is to be derived, the determination unit may determine that the reference line satisfying the predetermined accuracy is not capable of being derived and the derivation unit may derive the reference line on the basis of a pixel value of a region corresponding to the soft tissue between the gas region and the region corresponding to the bone tissue.

In the image processing apparatus according to the present disclosure, in a case in which the profile includes an artifact region caused by an artifact in a body of a subject from which at least one of the bone density or the bone mineral content is to be derived, the determination unit may determine that the reference line satisfying the predetermined accuracy is not capable of being derived.

In the image processing apparatus according to the present disclosure, in a case in which a position of a bone tissue used to derive at least one of the bone density or the bone mineral content is different from a predetermined position, the determination unit may determine that the reference line satisfying the predetermined accuracy is not capable of being derived.

In the image processing apparatus according to the present disclosure, the determination unit may determine whether the reference line is capable of being derived on the basis of a condition in which imaging conditions for generating the first radiographic image and the second radiographic image are predetermined.

In the image processing apparatus according to the present disclosure, the determination unit may determine whether the reference line satisfying the predetermined accuracy is capable of being derived on the basis of an inclination of the entire region corresponding to the soft tissue in the profile.

In the image processing apparatus according to the present disclosure, the determination unit may determine whether the reference line satisfying the predetermined accuracy is capable of being derived on the basis of whether a component caused by a scattered ray of the radiation is included in the pixel value of the region corresponding to the soft tissue in the profile.

In the image processing apparatus according to the present disclosure, in a case in which the determination unit determines that the reference line satisfying the predetermined accuracy is not capable of being derived, the derivation unit may remove the component caused by the scattered ray of the radiation from the pixel value of the predetermined region corresponding to the soft tissue on the basis of a predetermined scattered ray distribution model and derive the reference line.

In the image processing apparatus according to the present disclosure, in a case in which the determination unit determines that the reference line satisfying the predetermined accuracy is not capable of being derived, the derivation unit may derive the reference line, on the basis of a pixel value of a region corresponding to the soft tissue which is specified on the basis of at least one of a bone part difference image which is a difference image between the first radiographic image and the second radiographic image and in which the bone tissue is highlighted or a soft part difference image which is a difference image between the first radiographic image and the second radiographic image and in which the soft tissue is highlighted.

The image processing apparatus according to the present disclosure may further comprise a bone derivation unit that derives at least one of the bone mineral content or the bone density on the basis of a bone mass which is defined on the basis of the reference line in the region corresponding to the bone tissue.

In the image processing apparatus according to the present disclosure, each of the first and second radiation detectors may comprise a light emitting layer that is irradiated with the radiation and emits light. The plurality of pixels of each of the first and second radiation detectors may receive the light, generate the charge, and accumulate the charge. The light emitting layer of one of the first and second radiation detectors which is provided on an incident side of the radiation may include CsI and the light emitting layer of the other radiation detector may include GOS.

In order to achieve the object, the present disclosure provides a radiography system comprising: the image processing apparatus according to the present disclosure; and a radiography apparatus that outputs a first radiographic image and a second radiographic image to the image processing apparatus.

In order to achieve the object, the present disclosure provides an image processing method comprising: acquiring a first radiographic image generated by a first radiation detector irradiated with radiation with a first energy level and a second radiographic image generated by a second radiation detector irradiated with radiation with a second energy level different from the first energy level from a radiography apparatus including the first and second radiation detectors in which a plurality of pixels, each of which includes a conversion element that generates a larger amount of charge as it is irradiated with a larger amount of radiation, are arranged and which are arranged in a direction in which the radiation is emitted; and deriving a reference line which satisfies a predetermined accuracy for defining a bone mass, on the basis of a pixel value of a predetermined region corresponding to a soft tissue in a profile indicating a correspondence relationship between a pixel position and the pixel value in a derivation region including a region corresponding to the soft tissue and a region corresponding to a bone tissue in a difference image for derivation which is a difference image between the first radiographic image and the second radiographic image and is used to derive at least one of bone density or bone mineral content.

In order to achieve the object, the present disclosure provides an image processing method comprising: acquiring a first radiographic image generated by a single radiation detector irradiated with radiation with a first energy level and a second radiographic image generated by the radiation detector irradiated with radiation with a second energy level different from the first energy level from a radiography apparatus including the radiation detector in which a plurality of pixels, each of which includes a conversion element that generates a larger amount of charge as it is irradiated with a larger amount of radiation, are arranged; and deriving a reference line which satisfies a predetermined accuracy for defining a bone mass, on the basis of a pixel value of a predetermined region corresponding to a soft tissue in a profile indicating a correspondence relationship between a pixel position and the pixel value in a derivation region including a region corresponding to the soft tissue and a region corresponding to a bone tissue in a difference image for derivation which is a difference image between the first radiographic image and the second radiographic image and is used to derive at least one of bone density or bone mineral content.

In order to achieve the object, the present disclosure provides a non-transitory recording medium recording an image processing program that causes a computer to perform: acquiring a first radiographic image generated by a first radiation detector irradiated with radiation with a first energy level and a second radiographic image generated by a second radiation detector irradiated with radiation with a second energy level different from the first energy level from a radiography apparatus including the first and second radiation detectors in which a plurality of pixels, each of which includes a conversion element that generates a larger amount of charge as it is irradiated with a larger amount of radiation, are arranged and which are arranged in a direction in which the radiation is emitted; and deriving a reference line which satisfies a predetermined accuracy for defining a bone mass, on the basis of a pixel value of a predetermined region corresponding to a soft tissue in a profile indicating a correspondence relationship between a pixel position and the pixel value in a derivation region including a region corresponding to the soft tissue and a region corresponding to a bone tissue in a difference image for derivation which is a difference image between the first radiographic image and the second radiographic image and is used to derive at least one of bone density or bone mineral content.

In order to achieve the object, the present disclosure provides a non-transitory recording medium recording an image processing program that causes a computer to perform: acquiring a first radiographic image generated by a single radiation detector irradiated with radiation with a first energy level and a second radiographic image generated by the radiation detector irradiated with radiation with a second energy level different from the first energy level from a radiography apparatus including the radiation detector in which a plurality of pixels, each of which includes a conversion element that generates a larger amount of charge as it is irradiated with a larger amount of radiation, are arranged; and deriving a reference line which satisfies a predetermined accuracy for defining a bone mass, on the basis of a pixel value of a predetermined region corresponding to a soft tissue in a profile indicating a correspondence relationship between a pixel position and the pixel value in a derivation region including a region corresponding to the soft tissue and a region corresponding to a bone tissue in a difference image for derivation which is a difference image between the first radiographic image and the second radiographic image and is used to derive at least one of bone density or bone mineral content.

According to the present disclosure, it is possible to improve the accuracy of derivation of at least one of bone density or bone mineral content.

BRIEF DESCRIPTION OF THE DRAWINGS

Exemplary Embodiments of the present invention will be described in detail with reference to the following figures, wherein.

DETAILED DESCRIPTION

Hereinafter, embodiments of the present disclosure will be described in detail with reference to the drawings.

First Embodiment

Figure 1:
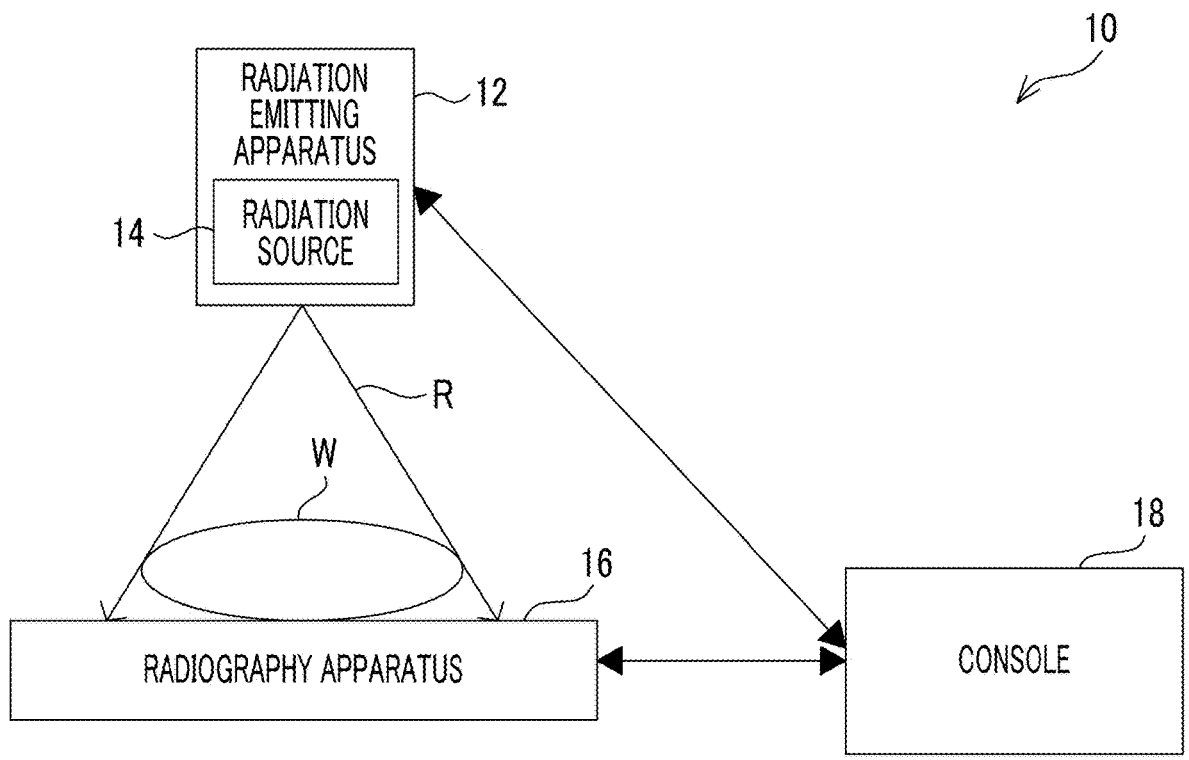
FIG. 1 is a block diagram illustrating an example of the configuration of a radiography system according to each embodiment.

First, the configuration of a radiography system 10 according to this embodiment will be described with reference to FIG. 1. As illustrated in FIG. 1, the radiography system 10 includes a radiation emitting apparatus 12, a radiography apparatus 16, and a console 18. In this embodiment, the console 18 is an example of an image processing apparatus according to the present disclosure.

The radiation emitting apparatus 12 according to this embodiment includes a radiation source 14 that irradiates a subject W, which is an example of an imaging target, with radiation R such as X-rays. An example of the radiation emitting apparatus 12 is a treatment cart. A method for commanding the radiation emitting apparatus 12 to emit the radiation R is not particularly limited. For example, in a case in which the radiation emitting apparatus 12 includes an irradiation button, a user, such as a radiology technician, may press the irradiation button to command the emission of the radiation R such that the radiation R is emitted from the radiation emitting apparatus 12. In addition, for example, the user, such as a radiology technician, may operate the console 18 to command the emission of the radiation R such that the radiation R is emitted from the radiation emitting apparatus 12.

When receiving the command to emit the radiation R, the radiation emitting apparatus 12 emits the radiation R from the radiation source 14 according to set exposure conditions, such as a tube voltage, a tube current, and an irradiation period. Hereinafter, the dose of the radiation R is simply referred to as "the amount of radiation".

Figure 2:
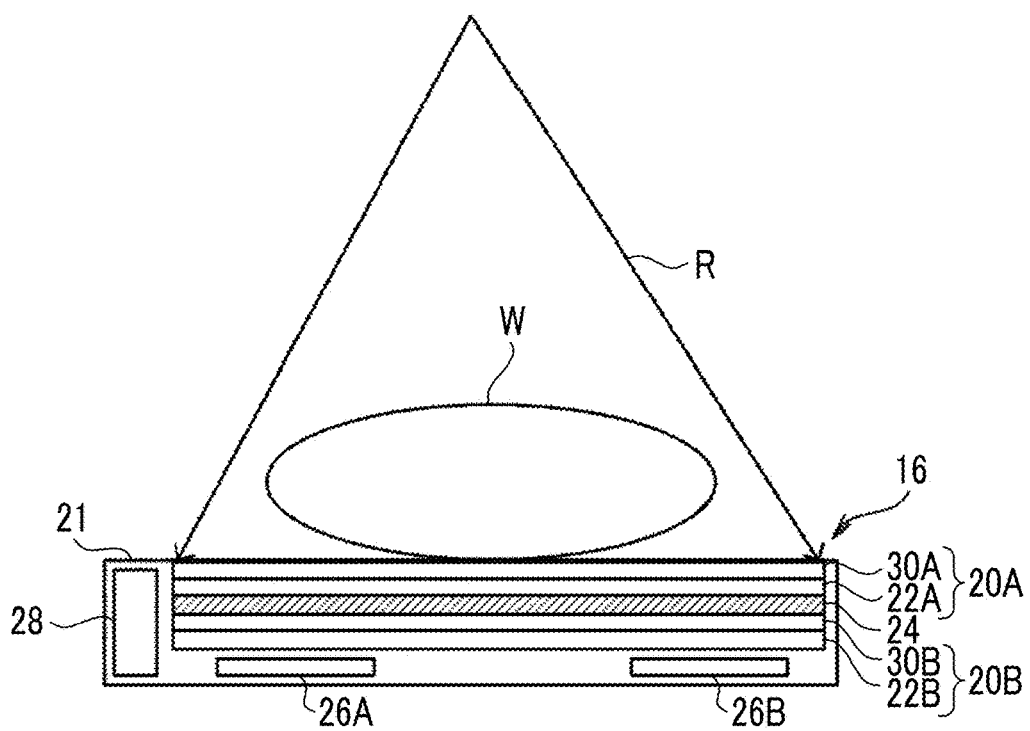
FIG. 2 is a side cross-sectional view illustrating an example of the configuration of a radiography apparatus according to a first embodiment.

Next, the configuration of the radiography apparatus 16 according to this embodiment will be described with reference to FIG. 2. As illustrated in FIG. 2, the radiography apparatus 16 includes a plate-shaped housing 21 that transmits the radiation R and has a waterproof, antibacterial, and airtight structure. The housing 21 includes a first radiation detector 20A and a second radiation detector 20B that detect the radiation R transmitted through the subject W. In addition, the housing 21 includes a radiation limitation member 24, a control substrate 26A, a control substrate 26B, and a case 28. The radiography apparatus 16 captures radiographic images of the subject W using the first radiation detector 20A and the second radiation detector 20B. Hereinafter, in a case in which the first radiation detector 20A and the second radiation detector 20B do not need to be distinguished from each other, they are generically referred to as "radiation detectors 20".

The first radiation detector 20A is provided on the incident side of the radiation R in the radiography apparatus 16 and the second radiation detector 20B is provided so as to be stacked on the side of the first radiation detector 20A from which the radiation R is transmitted and emitted. The first radiation detector 20A includes a thin film transistor (TFT) substrate 30A and a scintillator 22A which is an example of a light emitting layer that is irradiated with the radiation R and emits light. The TFT substrate 30A and the scintillator 22A are stacked in the order of the TFT substrate 30A and the scintillator 22A from the incident side of the radiation R. The term "stacked" means a state in which the first radiation detector 20A and the second radiation detector 20B overlap each other in a case in which the first radiation detector 20A and the second radiation detector 20B are seen from the incident side or the emission side of the radiation R in the radiography apparatus 16 and it does not matter how they overlap each other. For example, the first radiation detector 20A and the second radiation detector 20B, or the first radiation detector 20A, the radiation limitation member 24, and the second radiation detector 20B may overlap while coming into contact with each other or may overlap with a gap therebetween in the stacking direction.

The second radiation detector 20B includes a TFT substrate 30B and a scintillator 22B which is an example of the light emitting layer. The TFT substrate 30B and the scintillator 22B are stacked in the order of the TFT substrate 30B and the scintillator 22B from the incident side of the radiation R.

That is, the first radiation detector 20A and the second radiation detector 20B are so-called irradiation side sampling (ISS) radiation detectors that are irradiated with the radiation R from the side of the TFT substrates 30A and 30B.

In the radiography apparatus 16 according to this embodiment, the scintillator 22A of the first radiation detector 20A and the scintillator 22B of the second radiation detector 20B have different compositions. Specifically, for example, the scintillator 22A includes CsI (Tl) (cesium iodide having thallium added thereto) as a main component and the scintillator 22B includes gadolinium oxysulfide (GOS) as a main component. GOS has a higher sensitivity to the high-energy radiation R than CsI. In addition, a combination of the composition of the scintillator 22A and the composition of the scintillator 22B is not limited to the above-mentioned example and may be a combination of other compositions or a combination of the same compositions.

For example, the scintillators 22A and 22B have emission characteristics that vary depending on a thickness. As the thickness increases, the amount of light emitted increases and sensitivity increases. However, image quality deteriorates due to, for example, light scattering.

For example, in a case in which the scintillators 22A and 22B are formed by being filled with particles which are irradiated with the radiation R and emit light, such as GOS particles, as the diameter of the particle increases, the amount of light emitted increases and sensitivity increases. However, the amount of light scattering increases and the increase in the amount of light scattering affects adjacent pixels 32 (see FIG. 3), which results in the deterioration of image quality.

In addition, the scintillators 22A and 22B may have a stacked structure of a small-particle layer and a large-particle layer. For example, in a case in which each of the first radiation detector 20A and the second radiation detector 20B is irradiated with the radiation R from the scintillators 22A and 22B to the TFT substrates 30A and 30B unlike the radiography apparatus 16 according to this embodiment, image blurring is small in the scintillators 22A and 22B in which a region close to the irradiation side of the radiation R is filled with small particles and a region close to the side of the TFT substrate 30 that is the emission side of the radiation R is filled with large particles. However, oblique components of light that is radially emitted by the small particles are less likely to reach the TFT substrates 30A and 30B and sensitivity is reduced. In addition, in a case in which the ratio of the region filled with small particles to the region filled with large particles is changed such that the number of layers formed by the region filled with large particles is larger than the number of layers formed by the region filled with small particles, sensitivity increases. However, in this case, light scattering affects adjacent pixels 32, which results in the deterioration of image quality.

As the filling rate of the particles increases, the sensitivity of the scintillators 22A and 22B increases. However, the amount of light scattering increases and image quality deteriorates. Here, the filling rate is a value obtained by dividing the total volume of the particles of the scintillator 22A or 22B by the volume of the scintillator 22A or 22B and multiplying the divided value by 100 (the total volume of the particles of the scintillator 22A or 22B/the volume of the scintillator 22A or 22B×100). In addition, powder is treated in the scintillators 22A and 22B. Therefore, in a case in which the filling rate is greater than 80%, it is difficult to manufacture the scintillators 22A and 22B. For this reason, it is preferable that the filling rate is in the range of 50 vol % to 80 vol %.

In addition, the emission characteristics of the scintillators 22A and 22B vary depending on the doping amount of activator. As the doping amount of activator increases, the amount of light emitted tends to increase. However, the amount of light scattering increases and image quality deteriorates.

The emission characteristics of the scintillators 22A and 22B with respect to the radiation R vary depending on the material used for the scintillators 22A and 22B. For example, in a case in which each of the first radiation detector 20A and the second radiation detector 20B is irradiated with the radiation R from the scintillators 22A and 22B to the TFT substrates 30A and 30B unlike the radiography apparatus 16 according to this embodiment, the scintillator 22A is made of GOS and the scintillator 22B is made of CsI (Tl) in order to put emphasis on sensitivity in the scintillator 22A and to put emphasis on image quality in the scintillator 22B.

In addition, the emission characteristics of the scintillators 22A and 22B with respect to the radiation R vary depending on whether the scintillators 22A and 22B have a plate-shaped layer structure or a columnar separated layer structure.

For example, the scintillator 22A is configured to have the plate-shape layer structure and the scintillator 22B is configured to have the columnar separated layer structure in order to put emphasis on sensitivity in the scintillator 22A and to put emphasis on image quality in the scintillator 22B.

In a case in which reflecting layers that transmit the radiation R and reflect visible light are formed on the sides of the TFT substrates 30A and 30B which are opposite to the scintillators 22A and 22B, light generated by the scintillators 22A and 22B is more effectively guided to the TFT substrates 30A and 30B and sensitivity is improved. A method for forming the reflecting layer is not particularly limited. For example, any of a sputtering method, a vapor deposition method, and a coating method may be used to form the reflecting layer. It is preferable that the reflecting layer is made of a material with high reflectance in an emission wavelength range of the scintillators 22A and 22B used. For example, the reflecting layer is made of Au, Ag, Cu, Al, Ni, and Ti. For example, in a case in which the scintillators 22A and 22B are made of GOS:Tb, the reflecting layer is preferably made of Ag, Al, and Cu that have high reflectance in a wavelength of 400 nm to 600 nm. In a case in which the thickness of the reflecting layer is less than 0.01 µm, reflectance is not obtained. Even in a case in which the thickness is greater than 3 µm, the effect of further improving the reflectance is not obtained. For this reason, it is preferable that the thickness of the reflecting layer is in the range of 0.01 µm to 3 µm.

Therefore, the characteristics of the scintillators 22A and 22B may vary depending on a change in the diameter of particles, the multi-layered structure of the particles, the filling rate of the particles, the doping amount of activator, a material, a layer structure, and the formation of the reflecting layer.

The radiation limitation member 24 that limits the transmission of the radiation R is provided between the first radiation detector 20A and the second radiation detector 20B. An example of the radiation limitation member 24 is a plate-shaped member made of, for example, copper or tin. It is preferable that a variation in the thickness of the radiation limitation member 24 in the incident direction of the radiation R is equal to or less than 1% in order to uniformize the limitation (transmittance) of the radiation. In a case in which the first radiation detector 20A sufficiently absorbs the radiation R, the radiation limitation member 24 may not be provided.

The control substrate 26A is provided so as to correspond to the first radiation detector 20A and electronic circuits, such as an image memory 56A and a control unit 58A which will be described below, are formed on the control substrate 26A. The control substrate 26B is provided so as to correspond to the second radiation detector 20B and electronic circuits, such as an image memory 56B and a control unit 58B which will be described below, are formed on the control substrate 26B. The control substrate 26A and the control substrate 26B are provided on the side of the second radiation detector 20B which is opposite to the incident side of the radiation R.

The case 28 is provided at a position (that is, outside the range of an imaging region) that does not overlap the radiation detector 20 at one end of the housing 21. For example, a power supply unit 70 which will be described below is accommodated in the case 28. The installation position of the case 28 is not particularly limited. For example, the case 28 may be provided at a position that overlaps the radiation detector 20 on the side of the second radiation detector 20B which is opposite to the incident side of the radiation.

Next, the configuration of a main portion of an electric system of the radiography apparatus 16 according to this embodiment will be described with reference to FIG. 3.

Figure 3:
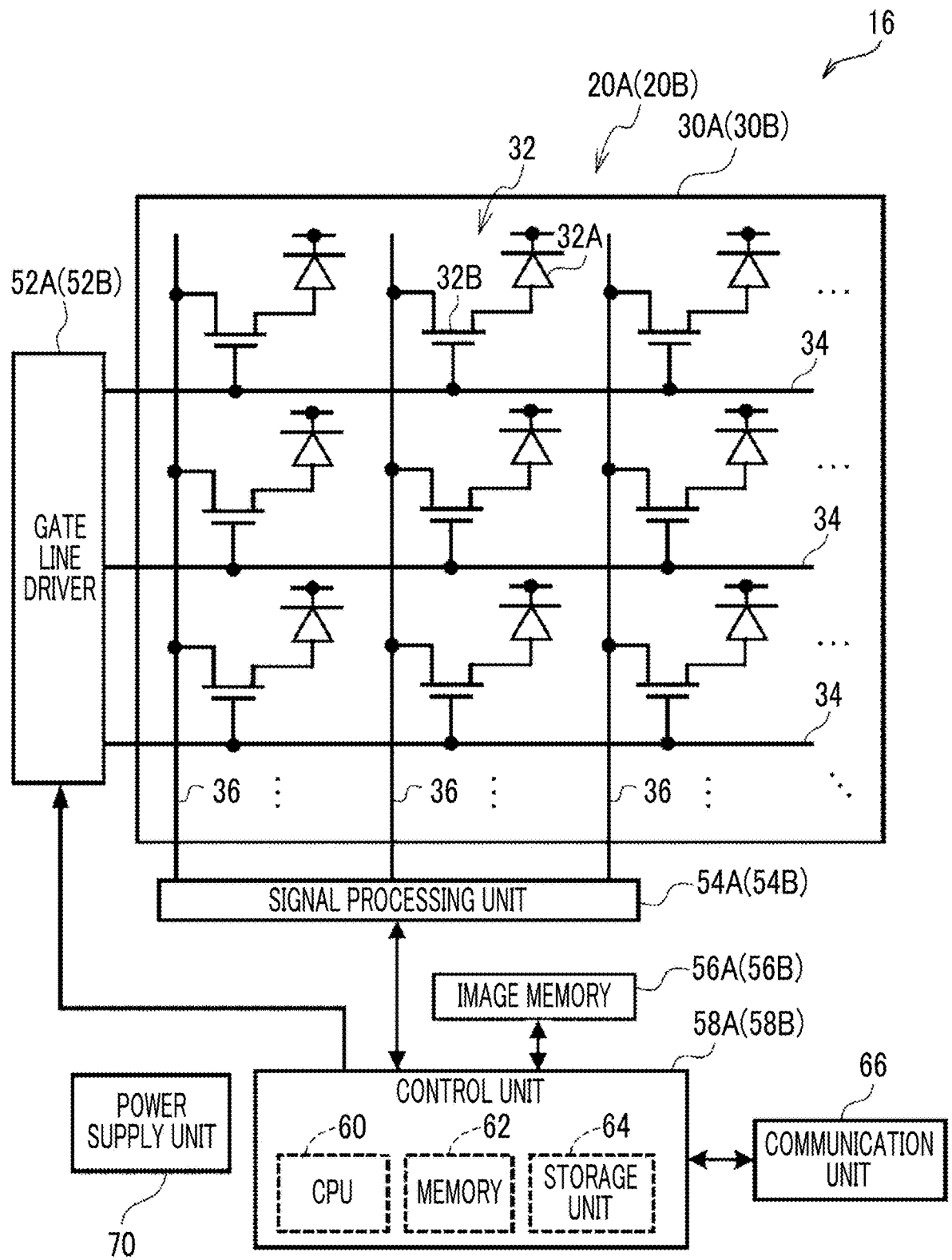
FIG. 3 is a block diagram illustrating an example of the configuration of a main portion of an electric system of a radiography apparatus according to each embodiment.

As illustrated in FIG. 3, a plurality of pixels 32 are two-dimensionally provided in one direction (a row direction in FIG. 3) and a cross direction (a column direction in FIG. 3) that intersects the one direction on the TFT substrate 30A. The pixel 32 includes a sensor unit 32A and a field effect thin film transistor (TFT; hereinafter, simply referred to as a "thin film transistor") 32B.

The sensor unit 32A includes, for example, an upper electrode, a lower electrode, and a photoelectric conversion film which are not illustrated, absorbs the light emitted from the scintillator 22A, generates charge, and accumulates the generated charge. The thin film transistor 32B reads the charge accumulated in the sensor unit 32A, converts the charge into an electric signal, and outputs the electric signal in response to a control signal. The sensor unit 32A is an example of a conversion element that generates a larger amount of charge as the amount of radiation becomes larger.

A plurality of gate lines 34 which extend in the one direction and are used to turn on and off each thin film transistor 32B are provided on the TFT substrate 30A. In addition, a plurality of data lines 36 which extend in the cross direction and are used to read out the charge through the thin film transistors 32B in an on state are provided on the TFT substrate 30A.

A gate line driver 52A is provided on one side of two adjacent sides of the TFT substrate 30A and a signal processing unit 54A is provided on the other side. Each gate line 34 of the TFT substrate 30A is connected to the gate line driver 52A and each data line 36 of the TFT substrate 30A is connected to the signal processing unit 54A.

The thin film transistors 32B corresponding to each gate line 34 on the TFT substrate 30A are sequentially turned on (in units of rows illustrated in FIG. 3 in this embodiment) by control signals which are supplied from the gate line driver 52A through the gate lines 34. Then, the charge which has been read by the thin film transistor 32B in an on state is transmitted as an electric signal through the data line 36 and is input to the signal processing unit 54A. In this way, charge is sequentially read from each gate line 34 (in units of rows illustrated in FIG. 3 in this embodiment) and image data indicating a two-dimensional radiographic image is acquired.

The signal processing unit 54A includes amplifying circuits (not illustrated) for amplifying an input electric signal and sample-and-hold circuits (not illustrated) which are provided for each data line 36. The electric signal transmitted through each data line 36 is amplified by the amplifying circuit and is then held by the sample-and-hold circuit. A multiplexer and an analog/digital (A/D) converter are connected to the output side of the sample-and-hold circuit in this order. The electric signals held by each sample-and-hold circuit are sequentially (serially) input to the multiplexer and are sequentially selected by the multiplexer. Then, the selected electric signal is converted into digital image data by the A/D converter.

The control unit 58A which will be described below is connected to the signal processing unit 54A. The image data output from the A/D converter of the signal processing unit 54A is sequentially output to the control unit 58A. The image memory 56A is connected to the control unit 58A. The image data sequentially output from the signal processing unit 54A is sequentially stored in the image memory 56A under the control of the control unit 58A. The image memory 56A has memory capacity that can store a predetermined amount of image data. Whenever a radiographic image is captured, captured image data is sequentially stored in the image memory 56A.

The control unit 58A includes a central processing unit (CPU) 60, a memory 62 including, for example, a read only memory (ROM) and a random access memory (RAM), and a non-volatile storage unit 64 such as a flash memory. An example of the control unit 58A is a microcomputer.

A communication unit 66 is connected to the control unit 58A and transmits and receives various kinds of information to and from external apparatuses, such as the radiation emitting apparatus 12 and the console 18, using at least one of wireless communication or wired communication. The power supply unit 70 supplies power to each of the above-mentioned various circuits or elements (for example, the gate line driver 52A, the signal processing unit 54A, the image memory 56A, the control unit 58A, and the communication unit 66). In FIG. 3, lines for connecting the power supply unit 70 to various circuits or elements are not illustrated in order to avoid complication.

Components of the TFT substrate 30B, the gate line driver 52B, the signal processing unit 54B, the image memory 56B, and the control unit 58B of the second radiation detector 20B have the same configurations as the corresponding components of the first radiation detector 20A and thus the description thereof will not be repeated here. In addition, the control unit 58A and the control unit 58B are connected such that they can communicate with each other.

With the above-mentioned configuration, the radiography apparatus 16 according to this embodiment captures radiographic images using the first radiation detector 20A and the second radiation detector 20B. Hereinafter, the radiographic image captured by the first radiation detector 20A is referred to as a "first radiographic image" and image data indicating the first radiographic image is referred to as "first radiographic image data". In addition, hereinafter, the radiographic image captured by the second radiation detector 20B is referred to as a "second radiographic image" and image data indicating the second radiographic image is referred to as "second radiographic image data".

Figure 4:
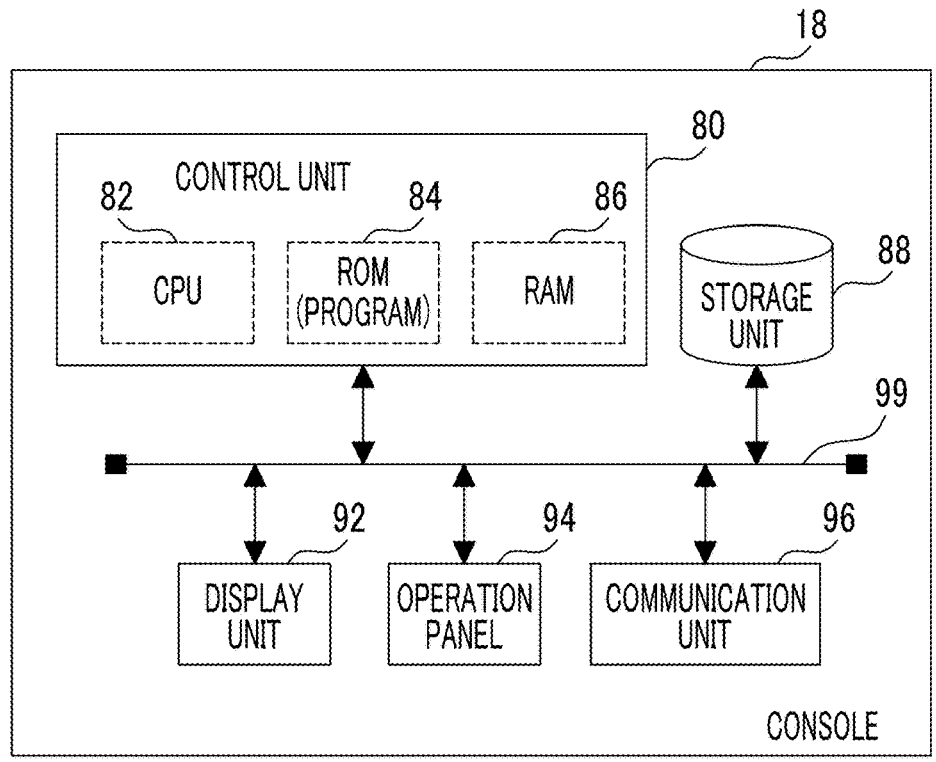
FIG. 4 is a block diagram illustrating an example of the configuration of a main portion of an electric system of a console according to each embodiment.

Next, the configuration of the console 18 according to this embodiment will be described with reference to FIG. 4. As illustrated in FIG. 4, the console 18 includes a control unit 80. The control unit 80 includes a CPU 82 that controls the overall operation of the console 18, a ROM 84 in which, for example, various programs or various parameters are stored in advance, and a RAM 86 that is used as, for example, a work area when the CPU 82 executes various programs.

In addition, the console 18 includes a non-volatile storage unit 88 such as a hard disk drive (HDD). The storage unit 88 stores and holds image data indicating the radiographic image captured by the first radiation detector 20A, image data indicating the radiographic image captured by the second radiation detector 20B, and various other data items.

The console 18 further includes a display unit 92, an operation unit 94, and a communication unit 96. The display unit 92 displays, for example, information related to imaging and a captured radiographic image. The operation unit 94 is used by a user to input a command to capture a radiographic image and a command to perform image processing for the captured radiographic image. For example, the operation unit 94 may have the form of a keyboard or the form of a touch panel integrated with the display unit 92. The communication unit 96 transmits and receives various kinds of information to and from the radiography apparatus 16 and the radiation emitting apparatus 12, using at least one of wireless communication or wired communication. In addition, the communication unit 96 transmits and receives various kinds of information to and from the external systems, such as a picture archiving and communication system (PACS) and a radiology information system (RIS), using at least one of wireless communication or wired communication.

The control unit 80, the storage unit 88, the display unit 92, the operation unit 94, and the communication unit 96 are connected to each other through a bus 99.

In the radiography apparatus 16 according to this embodiment, since the first radiation detector 20A and the radiation limitation member 24 absorb the radiation R, the amount of radiation that reaches the second radiation detector 20B is less than the amount of radiation that reaches the first radiation detector 20A. In addition, the radiation limitation member 24 generally has the characteristic that it absorbs a larger number of soft-ray components than hard-ray components in energy forming the radiation R, which depends on the material forming the radiation limitation member 24. Therefore, the energy distribution of the radiation R that reaches the second radiation detector 20B has a larger number of hard-ray components than the energy distribution of the radiation R that reaches the first radiation detector 20A.

In this embodiment, for example, about 50% of the radiation R that has reached the first radiation detector 20A is absorbed by the first radiation detector 20A and is used to capture a radiographic image. In addition, about 60% of the radiation R that has passed through the first radiation detector 20A and reached the radiation limitation member 24 is absorbed by the radiation limitation member 24. About 50% of the radiation R that has passed through the first radiation detector 20A and the radiation limitation member 24 and reached the second radiation detector 20B is absorbed by the second radiation detector 20B and is used to capture a radiographic image. Since the absorptivity of radiation by the radiation detector 20 and the radiation limitation member 24 varies depending on the energy of the radiation R, the shape of a spectrum changes.

That is, the amount of radiation used by the second radiation detector 20B to capture a radiographic image is about 20% of the amount of radiation used by the first radiation detector 20A to capture a radiographic image. In addition, the ratio of the amount of radiation used by the second radiation detector 20B to capture a radiographic image to the amount of radiation used by the first radiation detector 20A to capture a radiographic image is not limited to the above-mentioned ratio. However, it is preferable that the amount of radiation used by the second radiation detector 20B to capture a radiographic image is equal to or greater than 10% of the amount of radiation used by the first radiation detector 20A to capture a radiographic image in terms of diagnosis.

Figure 5:
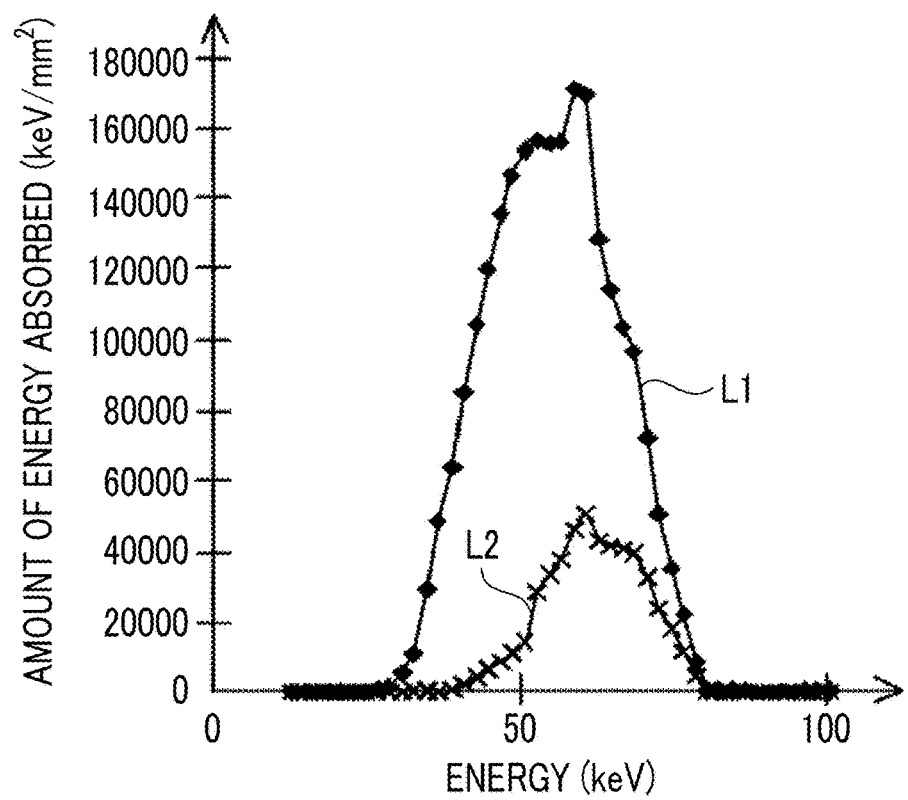
FIG. 5 is a graph illustrating the amount of radiation that reaches each of a first radiation detector and a second radiation detector.

Low-energy components of the radiation R are absorbed first. The radiation R absorbed by each of the first radiation detector 20A and the second radiation detector 20B will be described with reference to FIG. 5. In FIG. 5, the vertical axis indicates the amount of radiation R absorbed per unit area and the horizontal axis indicates the energy of the radiation R in a case in which the tube voltage of the radiation source 14 is 80 kV. In addition, in FIG. 5, a solid line L1 indicates the relationship between the energy of the radiation R absorbed by the first radiation detector 20A and the amount of radiation R absorbed per unit area. In addition, in FIG. 5, a solid line L2 indicates the relationship between the energy of the radiation R absorbed by the second radiation detector 20B and the amount of radiation R absorbed per unit area. Since the low-energy components of the radiation R are absorbed first, for example, as illustrated in FIG. 5, the energy components of the radiation R that reaches the second radiation detector 20B do not include the low-energy components of the energy components of the radiation R that reaches the first radiation detector 20A. That is, the energy of the radiation R emitted to the first radiation detector 20A is different from the energy of the radiation R emitted to the second radiation detector 20B through the first radiation detector 20A. Therefore, in the radiography apparatus 16 according to this embodiment, the radiation detectors 20 are irradiated with the radiations R having different energy levels and radiographic images are generated by the radiation detectors 20.

The console 18 according to this embodiment acquires radiographic image data generated by the radiation detectors 20 irradiated with the radiations R having different energy levels (radiation R with a first energy level and radiation R with a second energy level). In addition, the console 18 derives the ratio of the values of the corresponding pixels of first radiographic image data and second radiographic image data and generates image data for deriving the bone density of the subject W. Hereinafter, the image data for deriving the bone density of the subject W is referred to as "dual-energy X-ray absorptiometry (DXA) image data" and an image indicated by the DXA image data is referred to as a "DXA image". Specifically, the console 18 performs log conversion for each pixel value of each of the first radiographic image data and the second radiographic image data. Then, the console 18 subtracts image data obtained by performing log conversion for the second radiographic image data from image data obtained by performing log conversion for the first radiographic image data for each corresponding pixel to generate DXA image data. As such, the DXA image according to this embodiment is an example of a difference image for derivation according to the present disclosure.

Figure 6:
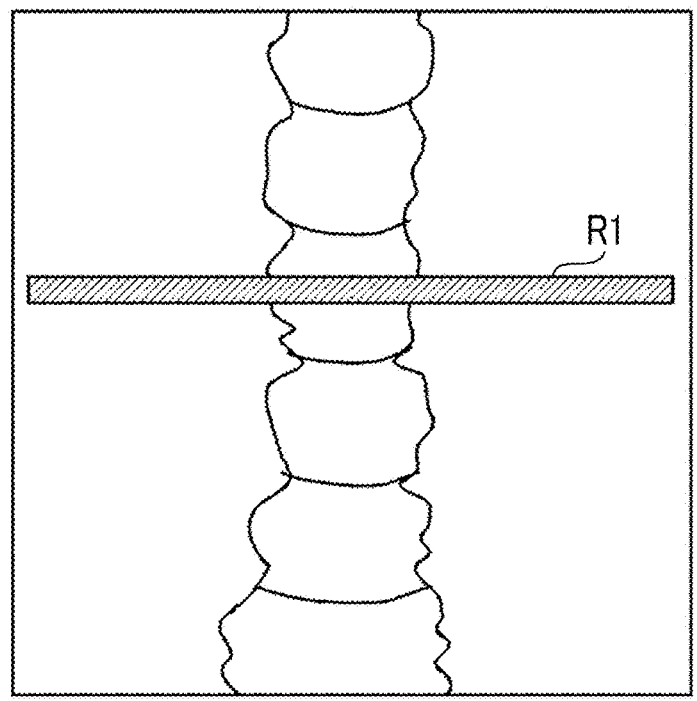
FIG. 6 is a front view illustrating an example of a region from which a DXA profile used to derive bone density is to be derived.

In addition, for example, as illustrated in FIG. 6, the console 18 according to this embodiment derives bone density from each pixel value (that is, the ratio of the values of the corresponding pixels of the first radiographic image and the second radiographic image) of the bone of the subject W in the cross-sectional direction (the horizontal direction in the example illustrated in FIG. 6) in the DXA image.

Figure 7:
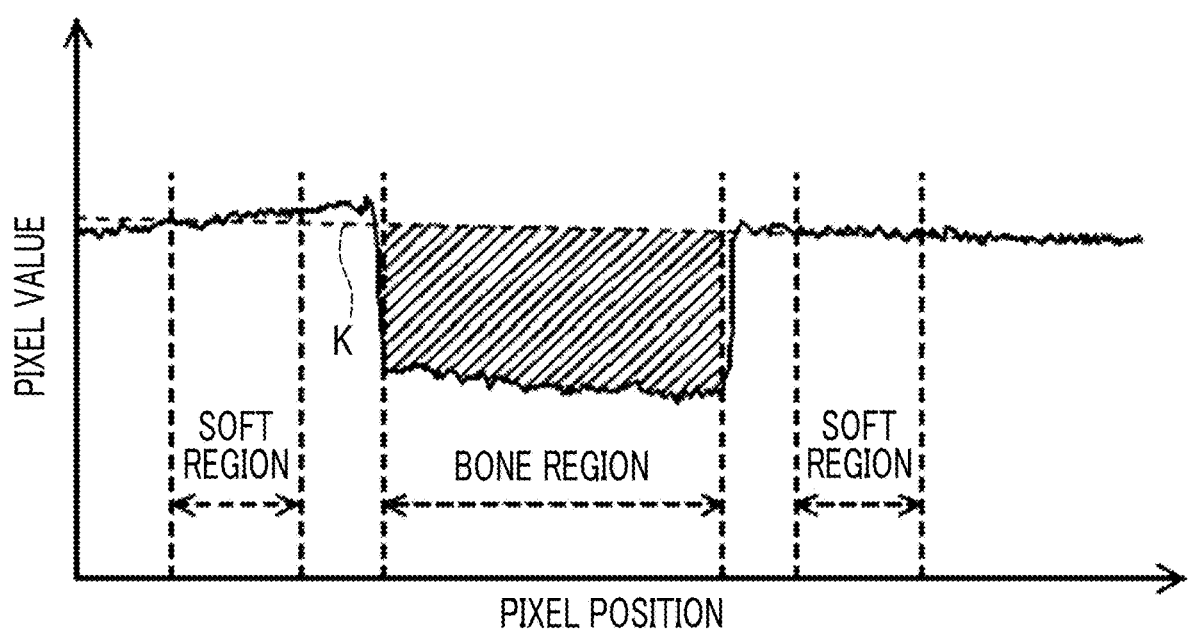
FIG. 7 is a graph illustrating a bone density derivation process.

FIG. 7 illustrates the value of each pixel in a derivation region R1 of the DXA image illustrated in FIG. 6. In FIG. 7, the horizontal axis indicates a pixel position in the horizontal direction of FIG. 6. In addition, in FIG. 7, the vertical axis indicates an average value of the values of a plurality of pixels in the vertical direction of FIG. 6 at each pixel position in the horizontal direction of FIG. 6. Hereinafter, a data group of the pixel values at each pixel position along the horizontal direction of FIG. 6 which is illustrated in FIG. 7 is referred to as a "DXA profile". In addition, a curve indicating the DXA profile is referred to as a profile curve (see a profile curve Pdxa in FIG. 9). That is, the DXA profile is a difference image between the first radiographic image and the second radiographic image and indicates the correspondence relationship between a pixel position and a pixel value in a derivation region R including a region corresponding to the soft tissues and a region corresponding to the bone tissues in the DXA image used to derive bone density. The DXA profile according to this embodiment is an example of a profile according to the present disclosure.

As illustrated in FIG. 7, for the pixel values in the DXA profile, a pixel value at a pixel position corresponding to the bone tissue of the subject W is less than a pixel value at a pixel position corresponding to the soft tissue. The console 18 according to this embodiment derives the average value of the pixel values in soft tissue regions (hereinafter, referred to as "soft regions") on both sides of a bone tissue region (hereinafter, referred to as a "bone region") and derives a straight line (hereinafter, referred to as a "reference line") K that connects the average values derived at the pixel positions in a central portion of each soft region. In addition, the console 18 adds the differences between the reference line K and the pixel values at each pixel position in the bone region to derive the area of the bone region (the area of a hatched portion illustrated in FIG. 7). The area is a value corresponding to the bone mass of the subject W. For example, the bone region is separated from the soft region by a predetermined number of pixels in FIG. 7 in order to prevent the influence of noise caused by rays scattered by the bone. In this embodiment, the "noise" is noise that is superimposed on image data indicating a radiographic image, such as the first radiographic image data or the second radiographic image data, by the influence of, for example, scattered rays or disturbance and includes a state in which the influence of the noise superimposed on the image appears in the image indicated by the image data and a state in which a sufficiently high signal/noise (S/N) ratio is not obtained since the amount of radiation R is small.

In addition, the console 18 divides the derived area by the number of pixels corresponding to the width of the bone region to derive the difference between the pixel values of the bone region and the soft region per unit number of pixels. The difference is a value corresponding to the bone density of the subject W. Then, the console 18 multiplies the derived difference between the pixel values of the bone region and the soft region per unit number of pixels by a predetermined unit conversion coefficient to derive the bone density of the subject W. In this embodiment, the pixel position of the derivation region R1 used to derive the DXA profile in the DXA image data, the pixel position of the soft region of the DXA profile, and the pixel position of the bone region are predetermined according to, for example, the subject W and an imaging part.

In the derivation of the bone density, for example, in a case in which noise is superimposed on the profile curve Pdxa or in a case in which gas generated in the body of the subject W is included in at least one of the first radiographic image or the second radiographic image (which will be described in detail below), the pixel value of the soft region is likely to be an inappropriate value. In a case in which the pixel value of the soft tissue is an inappropriate value, the reference line K which is a straight line connecting the derived average values at the pixel positions in the central portion of each soft region is likely to be inappropriate as described above. In a case in which the reference line K is inappropriate, the accuracy of derivation of the bone density is reduced and does not satisfy a predetermined accuracy.

For this reason, in this embodiment, in a case in which bone density is derived, the console 18 appropriately derive the reference line K to improve the accuracy of derivation of the bone density.

Next, the operation of the console 18 according to this embodiment when bone density is derived will be described.

Figure 8:
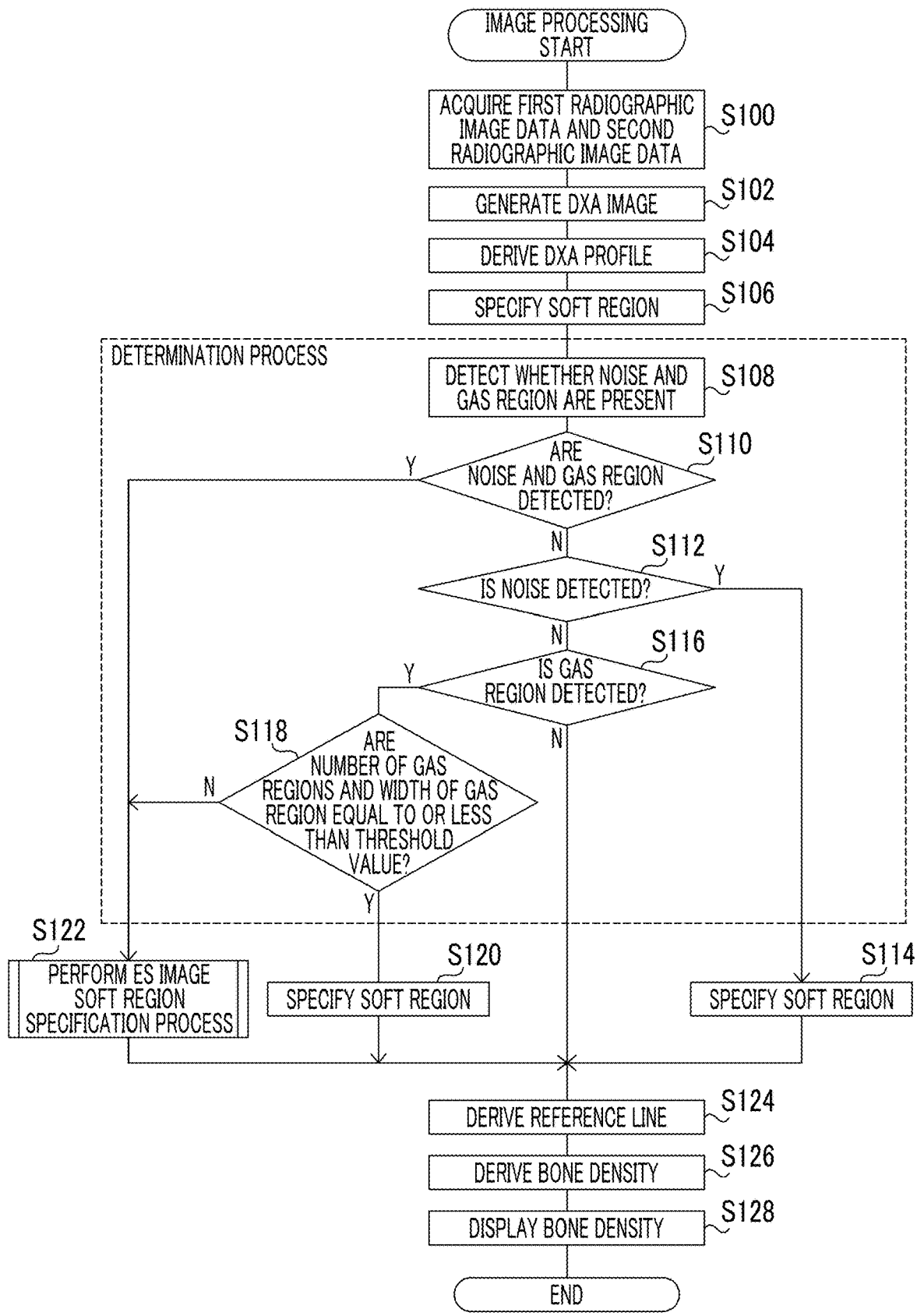
FIG. 8 is a flowchart illustrating an example of the flow of image processing performed by a control unit of a console according to the first embodiment.

FIG. 8 is a flowchart illustrating an example of the flow of image processing performed by the control unit 80 of the console 18 according to this embodiment. In a case in which the user inputs a command to derive bone density through the operation unit 94, the control unit 80 of the console 18 according to this embodiment executes an image processing program stored in the ROM 84 to perform the image processing illustrated in FIG. 8. In addition, in a case in which the CPU 82 of the control unit 80 according to this embodiment executes the image processing program, the control unit 80 according to this embodiment functions as an example of an acquisition unit, a determination unit, a derivation unit, and a bone derivation unit according to the present disclosure.

In Step S100 of FIG. 8, the control unit 80 acquires first radiographic image data and second radiographic image data. The acquisition destination of the first radiographic image data and the second radiographic image data is not particularly limited. For example, in a case in which the first radiographic image data and the second radiographic image data received from the radiography apparatus 16 have been stored in the storage unit 88 in advance, the control unit 80 may acquire the first radiographic image data and the second radiographic image data from the storage unit 88. In addition, for example, the control unit 80 may directly acquire the first radiographic image data and the second radiographic image data from the radiography apparatus 16.

Then, in Step S102, as described above, the control unit 80 generates DXA image data (DXA image) using the first radiographic image data and the second radiographic image. Then, in Step S104, as described above, the control unit 80 derives a DXA profile using the DXA image data.

Then, in Step S106, the control unit 80 specifies the soft tissues in the profile curve Pdxa of the DXA profile. As described above, the pixel position of the soft region in the DXA profile is predetermined according to, for example, an imaging part and the body thickness of the subject W. In this embodiment, information indicating the imaging part or the body thickness of the subject W is associated with the first radiographic image data and the second radiographic image data in advance and the control unit 80 acquires the first radiographic image data and the second radiographic image data in Step S100 and also acquires the information indicating the imaging part or the body thickness of the subject W. Then, the control unit 80 specifies the pixel position of a predetermined soft region on the basis of, for example, the body thickness of the subject W or the imaging part specified by the information indicating the imaging part to specify a soft region. Hereinafter, the predetermined soft region is referred to as an "initial soft region".

Then, in Step S108, the control unit 80 detects whether superimposed noise and a gas region corresponding to gas generated in the body of the subject W are present in the initial soft region of the profile curve Pdxa in the DXA profile. Steps S108 to S112, S116, and S118 in the image processing according to this embodiment are a process for determining whether bone density satisfying the predetermined accuracy is capable of being derived on the basis of the reference line K derived from the initial soft region and correspond to a determination process by a determination unit according to the present disclosure.

Figure 9:
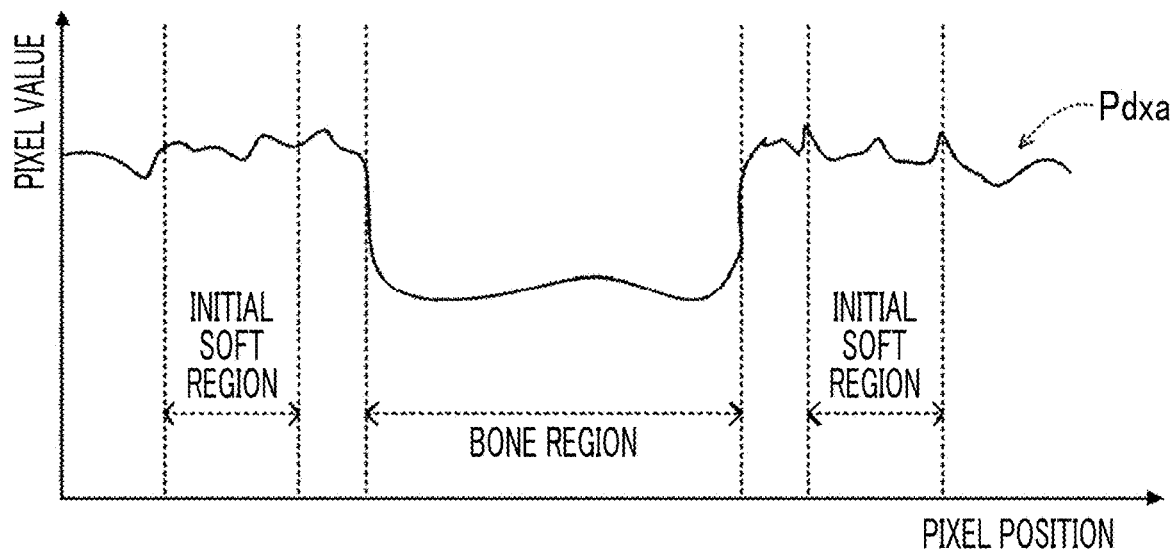
FIG. 9 is a graph illustrating an example of a profile curve (DXA profile) in a case in which noise is superimposed.

A method that is used by the control unit 80 to detect whether noise is superimposed on the initial soft region of the profile curve Pdxa in is not particularly limited. For example, in a case in which noise is superimposed on the initial soft region as illustrated in FIG. 9, a pixel value in the initial soft region of the profile curve Pdxa varies. For this reason, the control unit 80 may set a first threshold value for detecting the variation in the pixel value regarded as noise in advance. In a case in which the amplitude of the pixel value in the initial soft region of the DXA profile Pdxa is greater than the first threshold value, the control unit 80 may detect that noise is superimposed.

Figure 10:
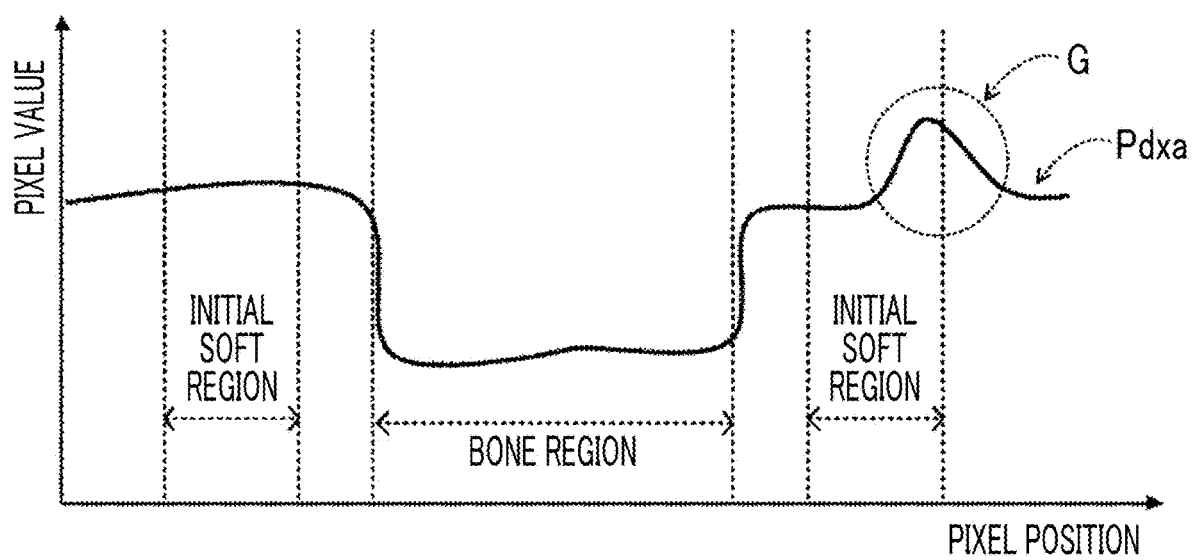
FIG. 10 is a graph illustrating an example of a profile curve in a case in which a gas region is included.

In addition, a method that is used by the control unit 80 to detect whether the gas region is present in the initial soft region of the profile curve Pdxa is not particularly limited. For example, in a case in which the initial soft region includes a gas region G as illustrated in FIG. 10, a protrusion that has a larger width than that in a case in which noise is superimposed is generated in the DXA profile Pdxa. Therefore, the control unit 80 may set a second threshold value for detecting the width of a region regarded as the gas region G of the DXA profile Pdxa in advance and detect the width of a region in which the pixel value increases by the predetermined second threshold value or more, decreases by the second threshold value or more, and is maintained. In a case in which the detected width is greater than the second threshold value, the control unit 80 may detect that the gas region G is generated.

Then, in Step S110, the control unit 80 determines whether both noise and the gas region G have been detected. In a case in which both noise and the gas region G have been detected, the determination result in Step S110 is "Yes" and the process proceeds to Step S122. The control unit 80 performs a soft region specification process using an ES image (Hereinafter, referred to as an "ES image soft region specification process") which will be described in detail below. In a case in which none of noise and the gas region G has been detected and in a case in which only one of noise and gas region G is detected, the determination result in Step S110 is "No" and the process proceeds to Step S112.

Then, in Step S112, the control unit 80 determines whether noise has been detected. In a case in which noise has been detected, the determination result in Step S112 is "Yes" and the process proceeds to Step S114.

Figure 11:
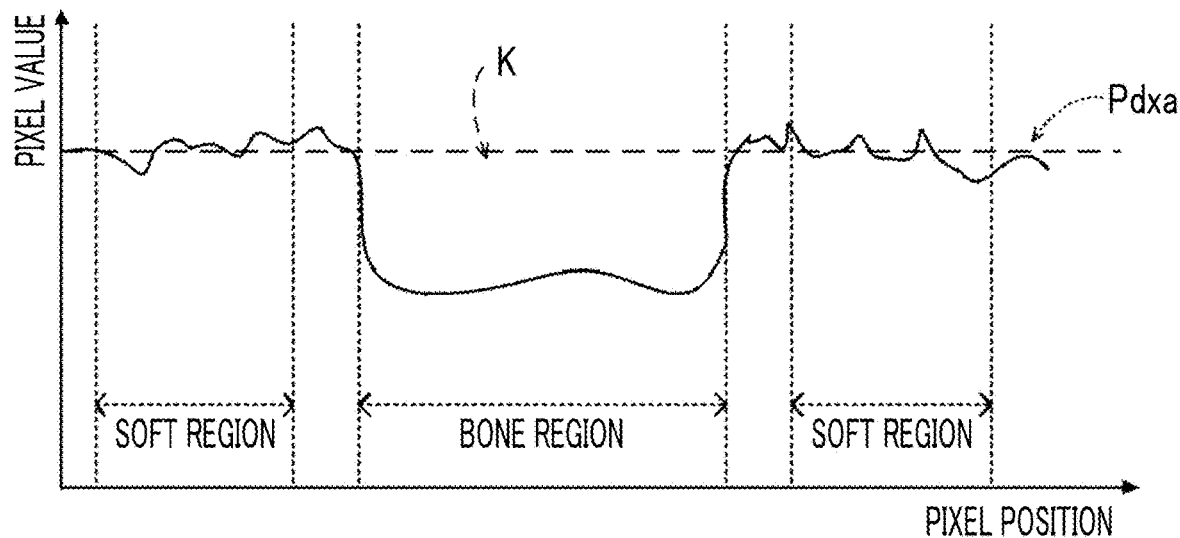
FIG. 11 is a diagram illustrating an example of the specification of a soft region in a case in which noise is superimposed.

Then, in Step S114, the control unit 80 specifies a soft region in the profile curve Pdxa and proceeds to Step S124. In this embodiment, in a case in which noise is superimposed on the profile curve Pdxa, for example, the control unit 80 increases the width of the soft region to be larger than the width of the initial soft region as illustrated in FIG. 11. In a case in which the width of the soft region is increased, noise is averaged and the influence of variation is prevented. An increase in the width of the soft region may be predetermined. For example, the increase in the width of the soft region may be predetermined according to, for example, an imaging part or the body thickness of the subject W.

On the other hand, in a case in which noise has not been detected, the determination result in Step S112 is "No" and the process proceeds to Step S116.

In Step S116, the control unit 80 determines whether the gas region G has been detected. In a case in which the gas region G has been detected, the determination result in Step S116 is "Yes" and the process proceeds to Step S118.

In Step S118, the control unit 80 determines whether each of the number of detected gas regions G and the width of the detected gas region G is equal to or less than a predetermined third threshold value. In this embodiment, in a case in which a plurality of gas regions G are included in the initial soft region or in a case in which the width of the gas region G is relatively large, the reference line K is derived using a newly specified soft region, without using the initial soft region. In a case in which the gas regions G are generated and the number of gas regions G is small or in a case in which the width of the gas region G is relatively small, the reference line K is derived using the initial soft region. In this embodiment, the third threshold value for determining whether to use the initial soft region is predetermined for each of the number of gas regions G and the width of the gas region G.

In a case in which each of the number of gas regions G and the width of the gas region G is equal to or less than the third threshold value, the determination result in Step S118 is "Yes" and the process proceeds to Step S120.

Figure 12:
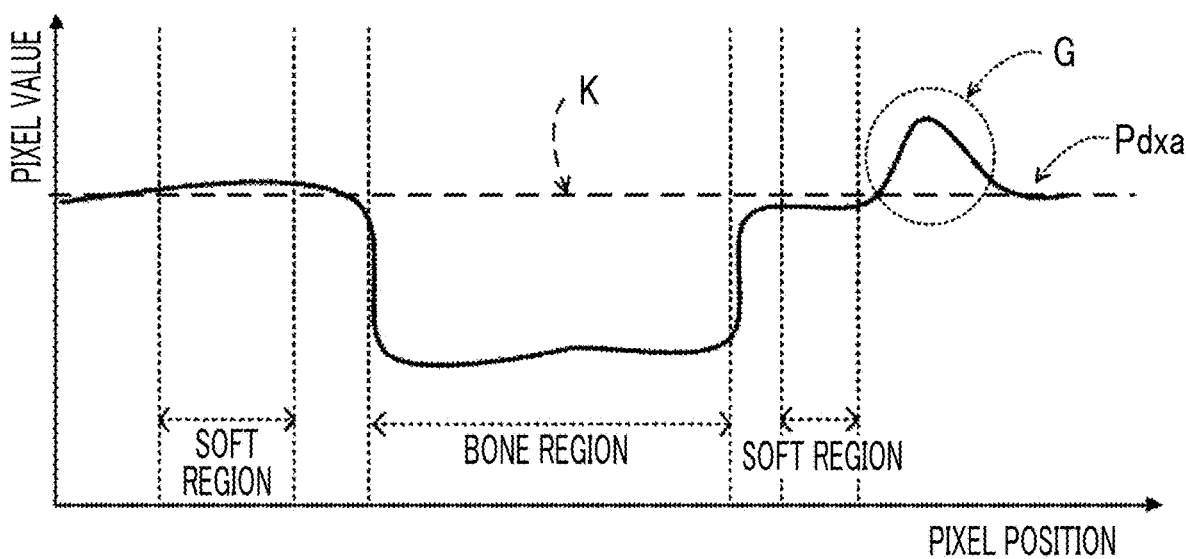
FIG. 12 is a diagram illustrating an example of the specification of the soft region in a case in which the gas region is included.

Then, in Step S120, the control unit 80 specifies a soft region in the profile curve Pdxa and proceeds to Step S124. In this embodiment, in a case in which the gas region G is generated in the profile curve Pdxa, for example, the control unit 80 specifies a region between the gas region G and the bone region as the soft region as illustrated in FIG. 12. In a case in which the gas region G is avoided, a variation in the profile curve Pdxa in the soft region is prevented. In addition, in a case in which the soft region is specified so as to avoid the gas region G, a variation in the pixel value in a region that is closer to the bone region than to the gas region G becomes more stable as in this embodiment. Therefore, a region that is closer to the bone region than to the gas region G is preferable as the soft region.

On the other hand, in a case in which each of the number of gas regions G and the width of the gas region G is greater than the third threshold value, the determination result in Step S118 is "No" and the process proceeds to Step S122.

Figure 13:
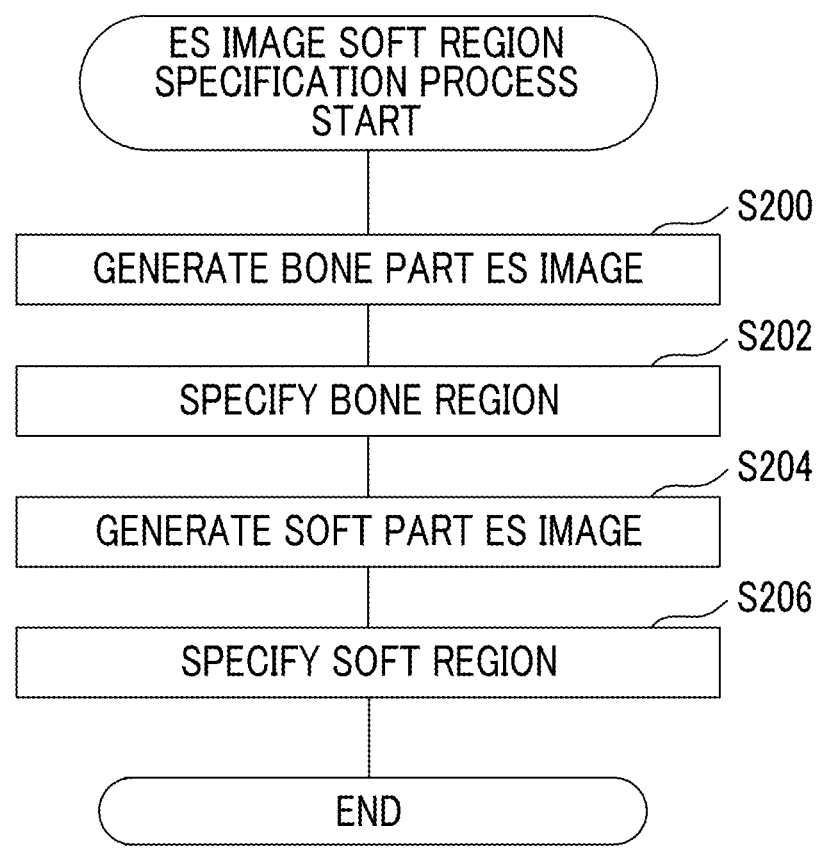
FIG. 13 is a flowchart illustrating an example of an ES image soft region specification process performed by the control unit according to the first embodiment.

Then, in Step S122, the control unit 80 performs the ES image soft region specification process. FIG. 13 is a flowchart illustrating an example of the flow of the ES image soft region specification process performed by the control unit 80 according to this embodiment.

In Step S200 illustrated in FIG. 13, the control unit 80 generates image data indicating a bone part energy subtraction image (hereinafter, referred to as an "ES image") in which the bone tissues have been highlighted. Hereinafter, the image data is referred to as "bone part ES image data". A method for generating the bone part ES image data is not particularly limited. For example, the control unit 80 may subtract image data obtained by multiplying the first radiographic image data by a predetermined coefficient for a bone part from image data obtained by multiplying the second radiographic image data by a predetermined coefficient for a bone part for each corresponding pixel to generate bone part ES image data indicating a bone part ES image in which the soft tissues have been removed and the bone tissues have been highlighted. As such, the bone part ES image according to this embodiment is an example of a bone part difference image according to the present disclosure.

Figure 14:
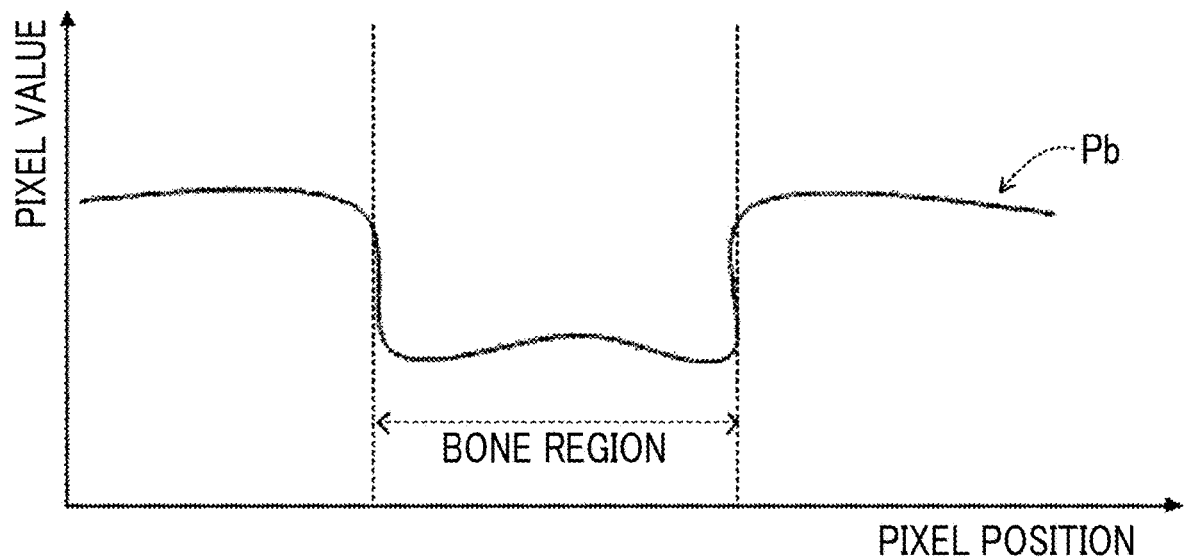
FIG. 14 is a diagram illustrating an example of the specification of a bone region using a profile curve of a bone part profile.

Then, in Step S202, the control unit 80 specifies a bone region. Specifically, the control unit 80 according to this embodiment derives a bone part profile from the bone part ES image, similarly to the derivation of the DXA profile from the DXA image. Then, for example, as illustrated in FIG. 14, the control unit 80 specifies a bone region using a profile curve Pb of the bone part profile. For example, as illustrated in FIG. 14, the bone part ES image is an image in which the bone tissues have been highlighted. Therefore, in the profile curve Pb obtained from the bone part ES image, a position corresponding to the bone tissue is clearer than that in the profile curve Pdxa obtained from the DXA image. In addition, since the influence of the gas region G is reduced, it is easy to specify the bone region.

Then, in Step S204, the control unit 80 generates image data (hereinafter, referred to as "soft part ES image data") indicating a soft part ES image in which the soft tissues have been highlighted. A method for generating the soft part ES image data is not particularly limited. For example, the control unit 80 may subtract image data obtained by multiplying the first radiographic image data by a predetermined coefficient for a soft part from image data obtained by multiplying the second radiographic image data by a predetermined coefficient for a soft part for each corresponding pixel to generate soft part ES image data indicating a soft part ES image in which the bone tissues have been removed and the soft tissues have been highlighted. Here, the soft part ES image data can be generated by the same method as that used to generate the bone part ES image data, using the predetermined coefficient for a soft part different from the predetermined coefficient for a bone part. As such, the soft part ES image according to this embodiment is an example of a soft part difference image according to the present disclosure.

Figure 15:
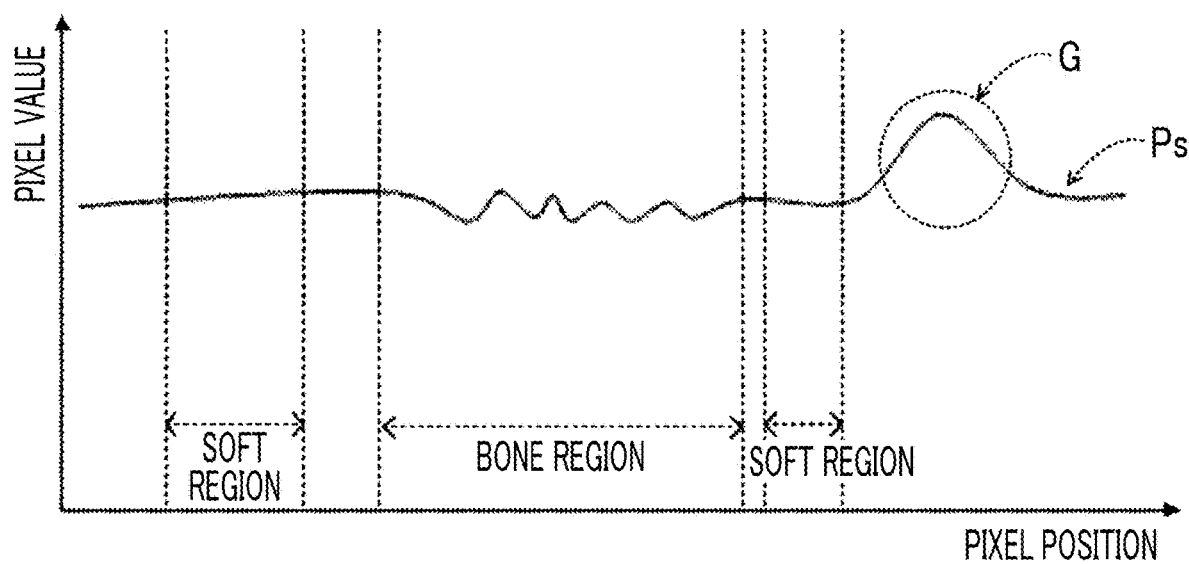
FIG. 15 is a diagram illustrating an example of the specification of a soft region using a profile curve of a soft part profile.

Then, in Step S206, the control unit 80 specifies a soft region. Specifically, the control unit 80 according to this embodiment derives a soft part profile from the soft part ES image, similarly to the derivation of the DXA profile from the DXA image. Then, for example, as illustrated in FIG. 15, the control unit 80 specifies a soft region using a profile curve Ps of the soft part profile. For example, as illustrated in FIG. 15, the soft part ES image is an image in which the soft tissues have been highlighted. Therefore, in the profile curve Ps obtained from the soft part ES image, a position corresponding to the soft tissue is clearer than that in the profile curve Pdxa obtained from the DXA image. In addition, since the gas region G is clear, it is easy to specify the soft tissue in a region other than the gas region G. For example, as illustrated in FIG. 15, the control unit 80 according to this embodiment specifies the soft region in a region other than the bone region derived in Step S202. It is preferable that the soft region is a region in which the amplitude of the pixel value in the profile curve Ps is small and which is considered to be flat. Here, the amplitude of the pixel value at which the profile curve Ps is considered to be flat may be predetermined according to, for example, the accuracy of detection of bone density.

In a case in which the soft region is specified in this way, the ES image soft region specification process in Step S122 of the image processing ends and the process proceeds to Step S124.

Figure 16:
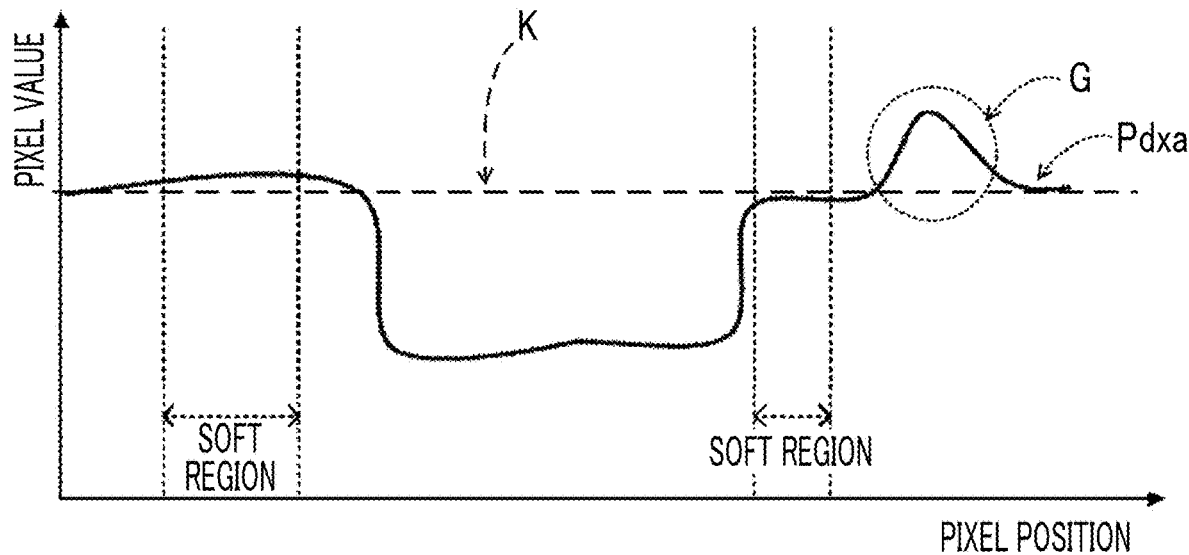
FIG. 16 is a diagram illustrating an example of the derivation of a reference line by the soft region specified by the soft part profile illustrated in FIG. 15.

In Step S124, for example, as illustrated in FIG. 16, the control unit 80 derives the reference line K, using the soft region specified by the ES image soft region specification process. Then, in Step S126, the control unit 80 derives bone density, using the reference line K derived in Step S124.

Then, in Step S128, the control unit 80 performs a control process of displaying the bone density derived in Step S126 on the display unit 92 and ends the image processing.

As such, in this embodiment, the control unit 80 of the console 18 determines whether bone density satisfying the predetermined accuracy is capable of being derived using the reference line K derived from the initial soft region of the profile curve Pdxa, on the basis of whether noise and the gas region G are superimposed on the profile curve Pdxa of the DXA profile. In a case in which the control unit 80 determines that the bone density is not capable of being derived, the control unit 80 specifies a region in which the influence of noise and the gas region G is prevented as the soft region and derives bone density, using the reference line K derived from the specified soft region.

With this configuration, according to the console 18 of this embodiment, it is possible to derive an appropriate reference line K. Therefore, it is possible to improve the accuracy of deriving bone density.

Figure 17:
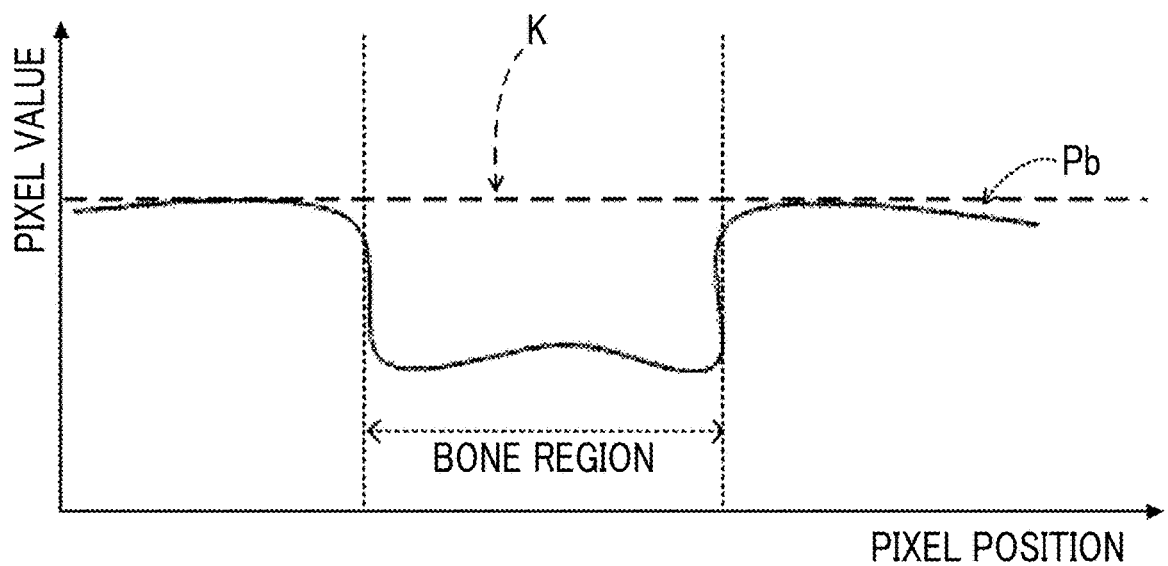
FIG. 17 is a diagram illustrating an example in which the reference line is derived from the bone part profile and the area of the bone region is derived.

In addition, the ES image soft region specification process is not limited to the above-mentioned process described in this embodiment and may be any process as long as it specifies the soft region on the basis of at least one of the bone part ES image or the soft part ES image. For example, the profile curve Pb of the bone part profile is derived from the bone part ES image generated in Step S200 of the ES image soft region specification process (see FIG. 13. Then, for example, as illustrated in FIG. 17, the reference line K is derived from the profile curve Pb and the area of the bone region is derived by the same method as that used to derive the bone density from the DXA image. As described above, each of the first radiographic image data and the second radiographic image data is multiplied by a predetermined coefficient for a bone part to generate the bone part ES image. Therefore, in some cases, the area of the bone region derived from the profile curve Pb is not equal to the area of the bone region derived from the profile curve Pdxa of the DXA profile. For this reason, a conversion coefficient for converting the area of the bone region derived from the profile curve Pb into the area of the bone region derived from the profile curve Pdxa is obtained by experiments in advance and the area of the bone region derived from the profile curve Pb is converted using the conversion coefficient to obtain an appropriate bone mass. In addition, instead of the configuration converting the area of the bone region, a conversion coefficient for converting the pixel value of the profile curve Pb into a pixel value corresponding to the profile curve Pdxa may be obtained, the pixel value of the profile curve Pb may be converted using the conversion coefficient, and the area of the bone region may be derived. The bone density of the subject W can be derived using the converted area of the bone region as described above.

Figure 18:
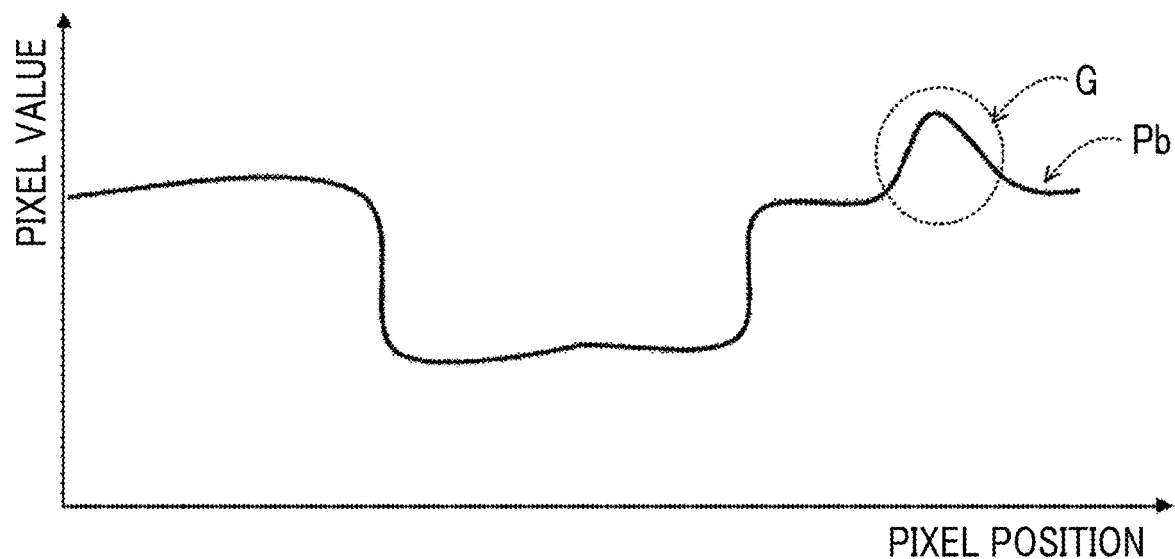
FIG. 18 is a diagram illustrating an example of a case in which the gas region is included in a profile curve of a bone part ES image.

For example, in a case in which gas is generated in the body of the subject W, for example, the gas region G is likely to be included in the profile curve Pb derived from the bone part ES image generated in Step S200 of the ES image soft region specification process (see FIG. 13) as illustrated in FIG. 18. For example, in a case in which the control unit 80 detects that the gas region G is present in the profile curve Ps of the soft part profile, using the same detection method as that used in Step S108 of the above-mentioned image processing (see FIG. 8), the control unit 80 specifies the position of the gas region G from the profile curve Ps derived from the soft part ES image generated in Step S204 of the ES image soft region specification process. A method for specifying the position of the gas region G from the profile curve Ps is not particularly limited. For example, the control unit 80 may detect the position of the gas region G, using the same method as that used in Step S108. Alternatively, the profile curve Ps may be displayed on the display unit 92 and the position of the gas region G designated by the user may be received through the operation unit 94. In addition, the control unit 80 changes the profile curve Pb on the basis of the specified position of the gas region G such that the pixel value of the gas region G is close to the pixel value of a region in the vicinity of the gas region G. The, for example, the same profile curve Ps as that illustrated in FIG. 17 is obtained. The method that is used by the control unit 80 to make the pixel value of the gas region G close to the pixel value of the region in the vicinity of the gas region G is not particularly limited. For example, a method that adjusts the predetermined coefficient for a bone part in the gas region G may be used. In a case in which this method is used, the predetermined coefficient for a bone part in the gas region G is different from the predetermined coefficient for a bone part in other regions.

Second Embodiment

In this embodiment, an aspect in which bone density is derived in a case in which the entire profile curve Pdxa (at least the entire initial soft region) of the DXA profile is inclined by the influence of scattered rays generated by radiation R which is direct rays incident on a radiography apparatus 16 and the inclination has an effect on the derivation of a reference line K will be described.

In some cases, for example, an image (a so-called omitted portion; hereinafter, referred to as a "direct ray portion") formed by direct rays of the radiation R which have reached the radiography apparatus 16 without passing through the subject W is generated in the first radiographic image and the second radiographic image acquired by the radiography apparatus 16.

For example, in general, bone density is derived using the first radiographic image and the second radiographic image in which the femur of the subject W is an imaging part. In a case in which the image of the femur is captured, the direct ray portion is included in the first radiographic image and the second radiographic image due to, for example, positioning.

Figure 19:
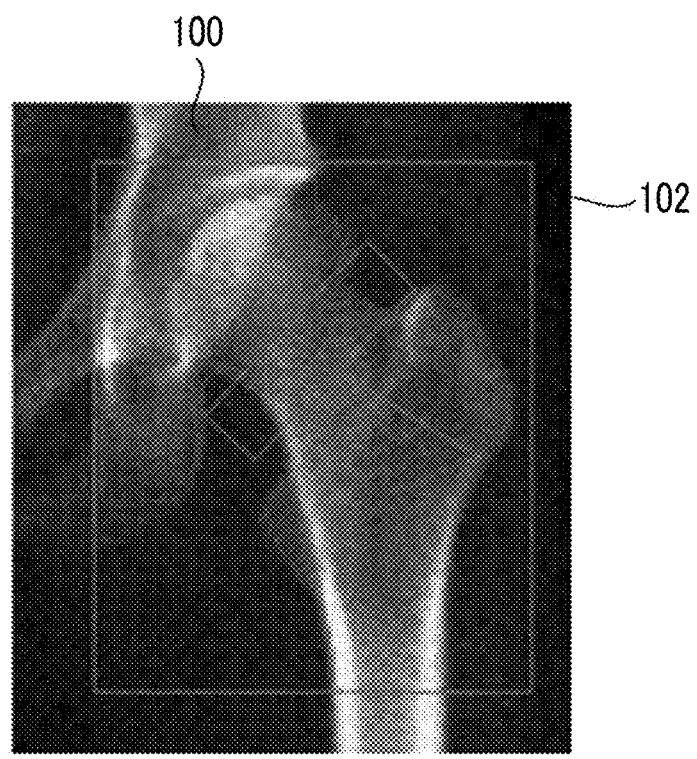
FIG. 19 is a diagram illustrating an example of a DXA image generated from a first radiographic image and a second radiographic image of the femur of the subject.

FIG. 19 illustrates an example of a DXA image generated from the first radiographic image and the second radiographic image of the femur of the subject W. For example, a direct ray portion image 102 is generated in the vicinity of a femur image 100 indicating the femur in the DXA image illustrated in FIG. 19. In a case in which many direct rays are generated and reach the radiography apparatus 16, the femur which is an imaging part is irradiated with scattered rays caused by the direct rays. For example, as illustrated in FIG. 20, the scattered rays have an effect on the DXA profile.

Figure 20:
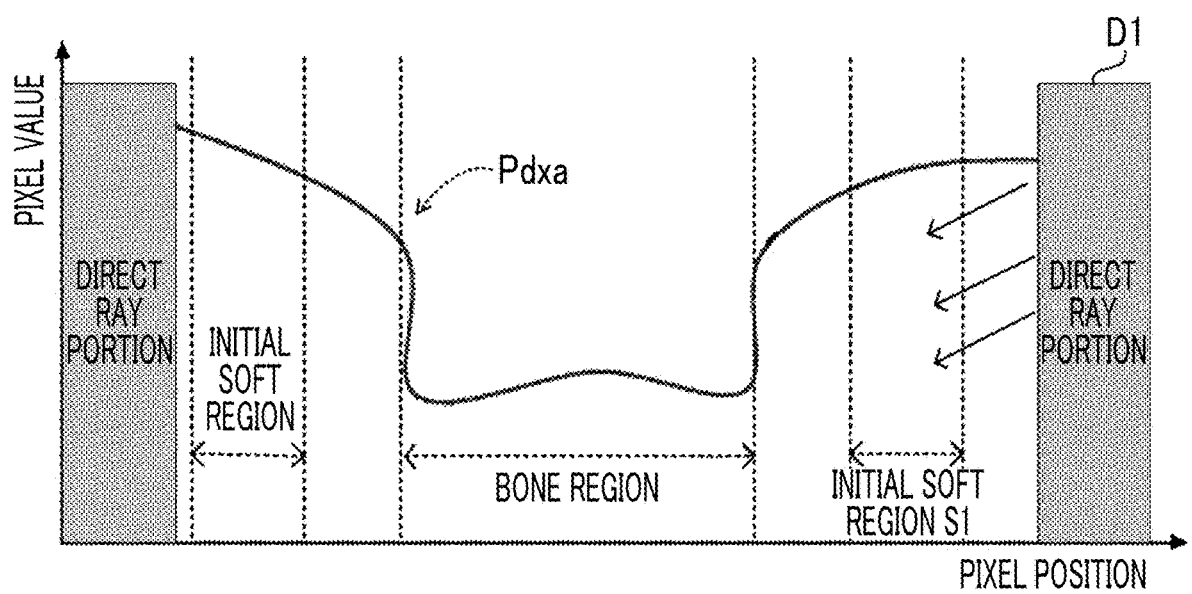
FIG. 20 is a flowchart illustrating an example of an ES image soft region specification process performed by a control unit according to a second embodiment.

In the example illustrated in FIG. 20, scattered ray components caused by a direct ray portion D1 are included in an initial soft region S1. Therefore, the profile curve Pdxa is inclined in the entire region from the bone region to the direct ray portion D1, particularly, in the initial soft region S1, and the pixel value increases from the bone region toward the direct ray portion D1.

In this case, since the pixel value of the initial soft region is inappropriate, the reference line K is inappropriate and the accuracy of derivation of the bone density is reduced and does not satisfy the predetermined accuracy.

For this reason, in this embodiment, in a case in which bone density is derived, the console 18 reduces the influence of scattered rays and appropriately derives the reference line K to improve the accuracy of derivation of the bone density.

Since the configuration of a radiography system 10 according to this embodiment is the same as that of the radiography system 10 (see FIGS. 1 to 4) according to the first embodiment, the description thereof will not be repeated. In this embodiment, since image processing performed by the control unit 80 of the console 18 is partially different from the image processing (see FIG. 8) according to the first embodiment, the image processing performed by the control unit 80 according to this embodiment will be described.

Figure 21:
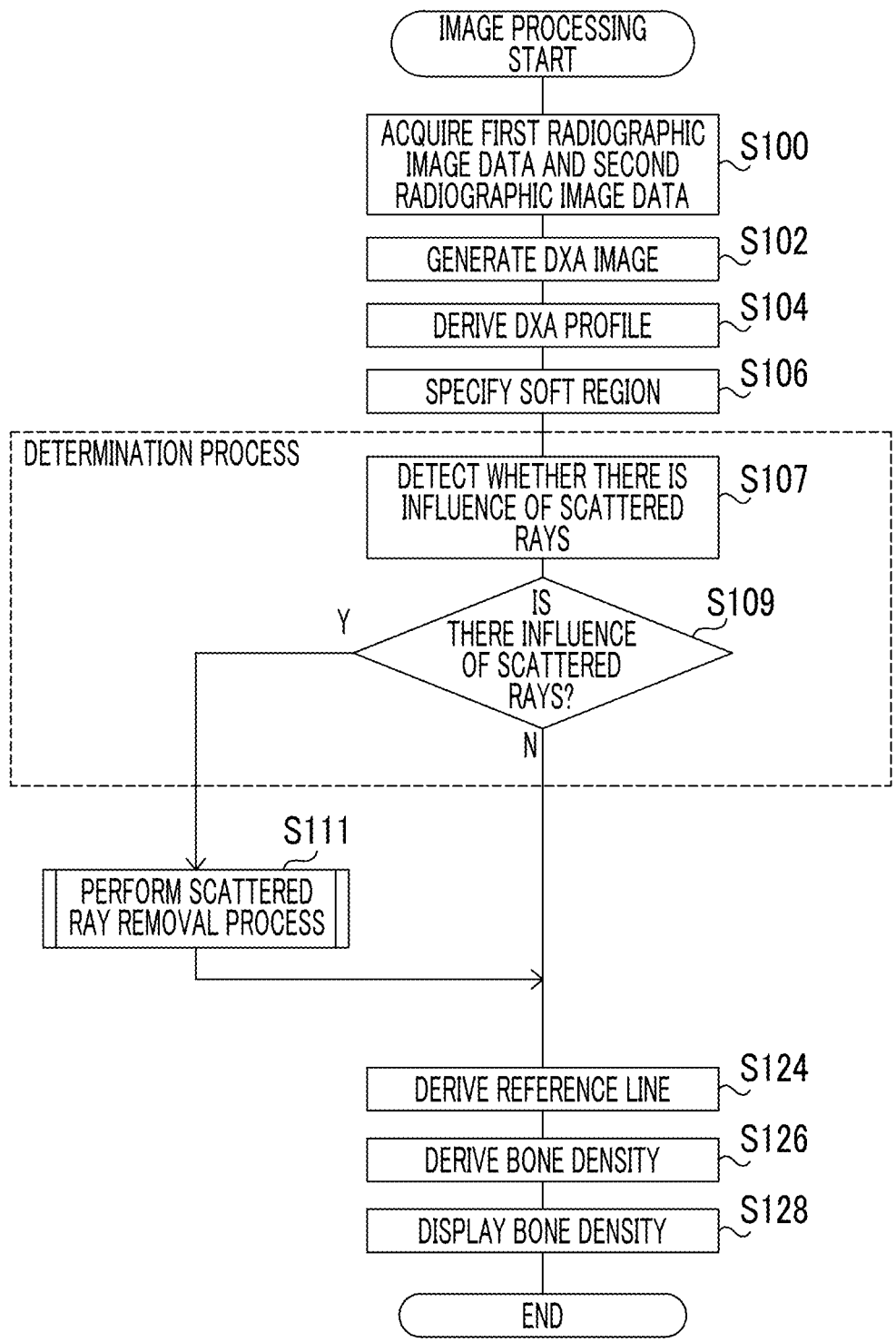
FIG. 21 is a flowchart illustrating an example of image processing performed by the control unit according to the second embodiment.

FIG. 21 is a flowchart illustrating an example of the flow of the image processing performed by the control unit 80 of the console 18 according to this embodiment. As illustrated in FIG. 21, the image processing according to this embodiment is different from the image processing (see FIG. 8) according to the first embodiment in that Steps S107 to S111 are performed instead of Steps S108 to S122.

As illustrated in FIG. 21, in Step S107, the control unit 80 detects whether there is influence of scattered rays in the initial soft region of the profile curve Pdxa of the DXA profile. A method that is used by the control unit 80 to detect whether there is influence of the scattered rays in the initial soft region is not particularly limited. For example, in a case in which there is influence of the scattered rays as illustrated in FIG. 20, the profile curve Pdxa is inclined in the initial soft region S1. Therefore, the inclination of the profile curve Pdxa in the initial soft region S1 is detected and a fourth threshold value for detecting the influence of the scattered rays is predetermined. In a case in which the inclination of the profile curve Pdxa in the initial soft region S1 detected by the control unit 80 is equal to or greater than the fourth threshold value, it may be detected that there is influence of noise. In addition, for example, whether there is influence of scattered rays may be detected on the basis of the area of the direct ray portion or the distance from the direct ray portion to a measurement position.

Step S107 and S109 in the image processing according to this embodiment are a process for determining whether bone density satisfying a predetermined accuracy is capable of being derived, on the basis of the reference line K derived from the initial soft region and correspond to a determination process by a determination unit according to the present disclosure.

Then, in Step S109, the control unit 80 determines whether the influence of the scattered rays has been detected. In a case in which the influence of the scattered rays has not been detected, the determination result in Step S109 is "No" and the process proceeds to Step S124. On the other hand, in a case in which the influence of the scattered rays has been detected, the determination result in Step S109 is "Yes" and the process proceeds to Step S111.

Figure 22:
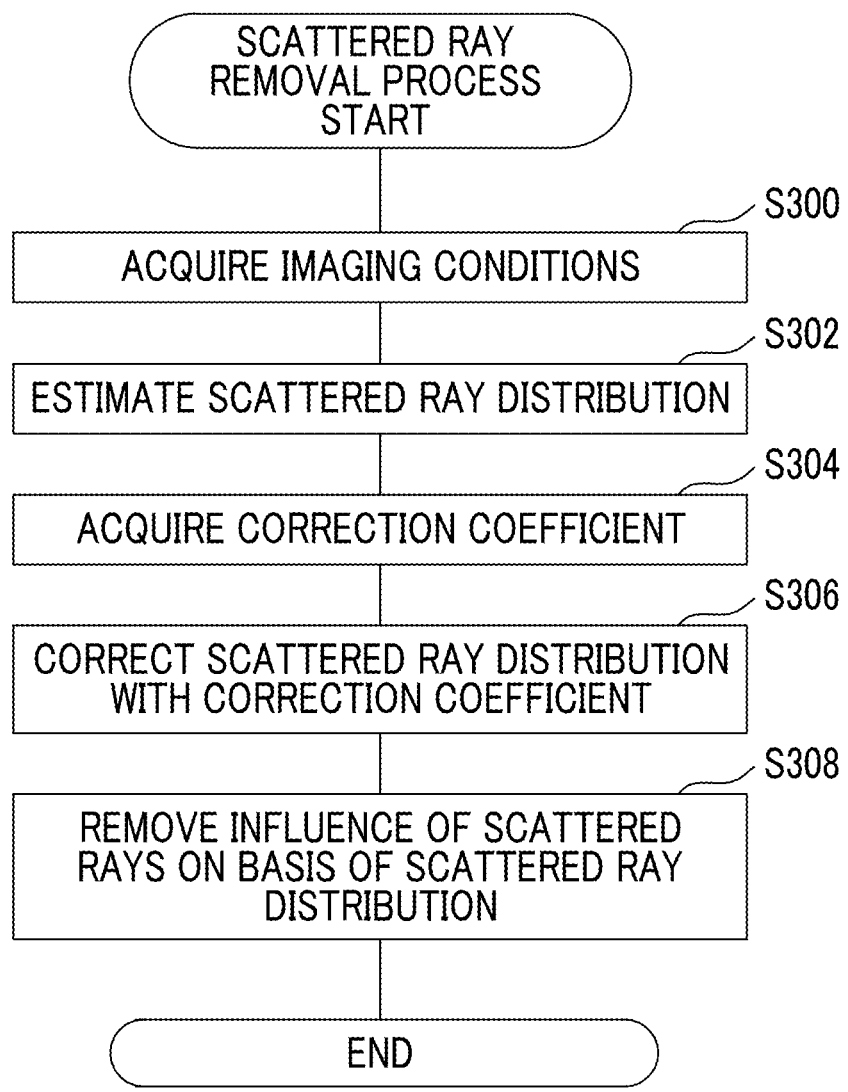
FIG. 22 is a flowchart illustrating an example of a scattered ray removal process performed by the control unit according to the second embodiment.

In Step S111, the control unit 80 performs a scattered ray removal process. FIG. 22 is a flowchart illustrating an example of the flow of the scattered ray removal process performed by the control unit 80 according to this embodiment.

In Step S300, the control unit 80 acquires imaging conditions in a case in which the first radiographic image and the second radiographic image are captured. Here, the imaging conditions acquired by the control unit 80 have an effect on the scattered rays and include, for example, a tube voltage and a tube current.

A method that is used by the control unit 80 to acquire the imaging conditions is not particularly limited. For example, in a case in which the imaging conditions are associated with the first radiographic image data and the second radiographic image data in advance, the imaging conditions are acquired in Step S100, in addition to the first radiographic image data and the second radiographic image data. For example, the control unit 80 may acquire the imaging conditions designated by the user through the operation unit 94.

Then, in Step S302, the control unit 80 estimates a distribution of the scattered rays. For example, the control unit 80 according to this embodiment estimates the distribution of the scattered rays, using a scattered ray model illustrated in FIG. 23. For example, in the scattered ray model illustrated in FIG. 23, an imaging surface 29 of the housing 21 according to this embodiment which is irradiated with the radiation R is irradiated with the radiation R which is a direct ray and each of the first radiation detector 20A and the second radiation detector 20B is irradiated with scattered rays X that are incident from a pinhole 42 provided in the imaging surface 29 through a grid 40 that is made of, for example, lead for removing scattered rays. The distribution of the scattered rays X emitted to each of the first radiation detector 20A and the second radiation detector 20B is measured in advance and is stored as a scattered ray distribution model in, for example, the storage unit 88 in advance.

The control unit 80 reads out the scattered ray distribution model from the storage unit 88, detects the region of the direct ray portion from the soft part ES image, and integrates the values of the scattered rays obtained by the scattered ray distribution model according to the region of the direct ray portion to estimate a scattered ray distribution in the soft part ES image. A method that is used by the control unit 80 to detect the region of the direct ray portion is not particularly limited. For example, a fifth threshold value for detecting the region of the direct ray portion may be predetermined. In a case in which the number of pixels which have a value greater than the fifth threshold value and are adjacent to each other is equal to or greater than the fifth threshold value, the control unit 80 may detect a region including the pixels as the direct ray portion.

Then, in Step S304, the control unit 80 acquires a correction coefficient. In general, the distribution of the scattered rays varies depending on, for example, the grid 40 used for imaging or the film thickness of the scintillators 22A and 22B. Therefore, the console 18 experimentally obtains a correspondence relationship between the correction coefficient and the type and position of the grid 40 or the film thickness of the scintillators 22A and 22B which is a factor changing the distribution of the scattered rays and stores the correspondence relationship in, for example, the storage unit 88 in advance. Therefore, in Step S304, the control unit 80 acquires the correction coefficient from the storage unit 88. Then, in Step S306, the control unit 80 corrects the distribution of the scattered rays estimated in Step S302 with the read-out correction coefficient.

Then, in Step S308, the control unit 80 removes the influence of the scattered rays from the DXA image on the basis of the distribution of the scattered rays corrected in Step S306, ends the scattered ray removal process, and proceeds to Step S124 of the image processing.

Figure 23:
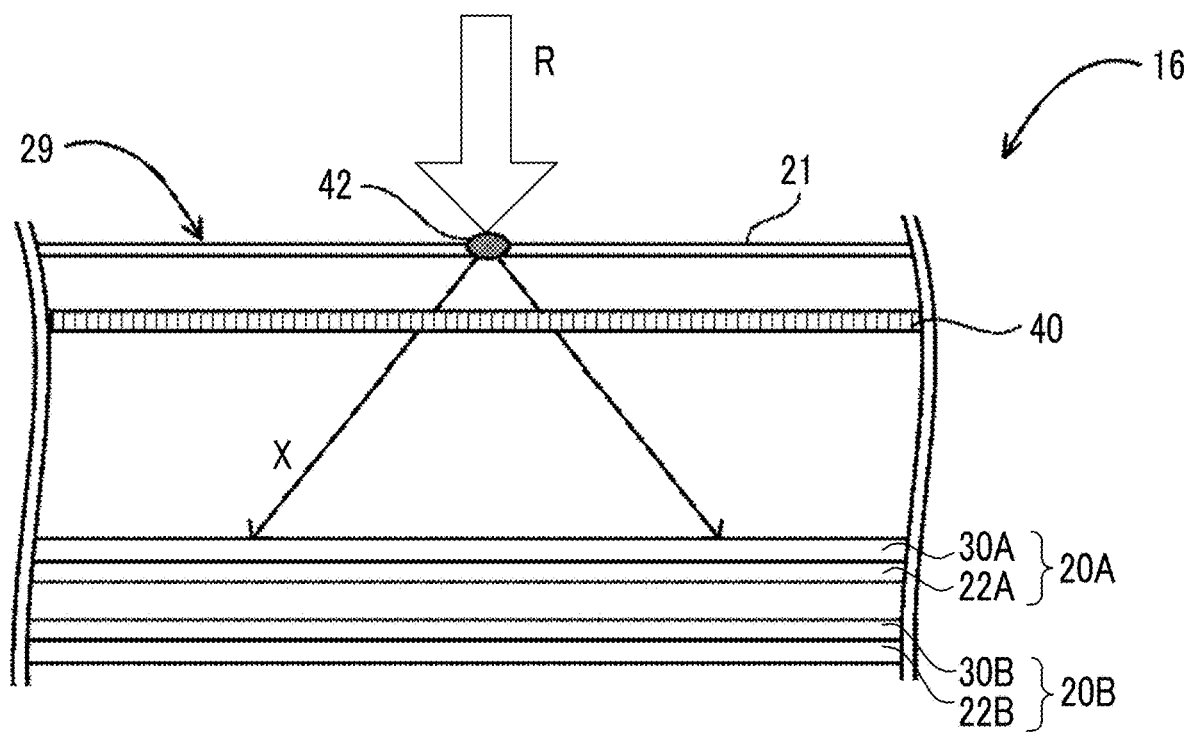
FIG. 23 is a diagram illustrating an example of a scattered ray model.

The scattered ray removal process performed in Step S111 of the image processing is not limited to the process illustrated as an example in the flowchart in FIG. 23 and other methods may be used.

As such, in this embodiment, in a case in which a component caused by the influence of the scattered rays is included in the profile curve Pdxa of the DXA profile, particularly, in the initial soft region, the control unit 80 of the console 18 determines that bone density satisfying the predetermined accuracy is not capable of being derived, removes the component caused by the influence of the scattered rays, and derives bone density on the basis of the reference line K derived from the initial soft region.

Therefore, according to the console 18 of this embodiment, it is possible to derive an appropriate reference line K and thus to improve the accuracy of deriving bone density.

As described above, in each of the above-described embodiments, the control unit 80 of the console 18 acquires the first radiographic image data and the second radiographic image data and derives the reference line K which satisfies a predetermined accuracy for defining a bone mass, on the basis of the pixel value of the initial soft region in the DXA profile indicating the correspondence relationship between the pixel position and the pixel value of the derivation region R1 having the soft region and the bone region in the DXA image which is a difference image between the first radiographic image and the second radiographic image and is used to derive at least one of bone density or bone mineral content.

In some cases, the accuracy of derivation is reduced in the derivation of bone density or bone mineral content using the DXA profile. The examination results of the inventor prove that the cause of the reduction in the accuracy of derivation is the derivation of an inappropriate reference line K. In a case in which the reference line is derived from the region corresponding to the soft tissue and, for example, there is influence of noise or gas is generated in the body of the subject, the pixel value of the region corresponding to the soft tissue for deriving the reference line K is likely to be an inappropriate value. In this case, an appropriate reference line is not likely to be derived. In a case in which bone density or bone mineral content is derived using the inappropriate reference line K, the accuracy of derivation of the bone density or the bone mineral content is reduced.

In contrast, according to the console 18 of each of the above-described embodiments, it is possible to derive an appropriate reference line K and thus to improve the accuracy of derivation of bone density.

In each of the above-described embodiments, the control unit 80 of the console 18 determines whether the reference line K satisfying the predetermined accuracy is capable of being derived. In a case in which the control unit 80 determines that the reference line K is capable of being derived, the control unit 80 derives the reference line. In each of the above-described embodiments, in a case in which the control unit 80 of the console 18 determines that the reference line K satisfying the predetermined accuracy is not capable of being derived, the control unit 80 specifies a region satisfying the predetermined accuracy as the soft region and derives bone density, using the reference line K derived from the specified soft region.

Therefore, it is possible to derive an appropriate reference line K and thus to improve the accuracy of derivation of bone density.

For example, in a case in which noise is superimposed on the profile curve Pdxa of the DXA profile or the gas region G is included in the profile curve Pdxa, the noise and the gas region G vary whenever the first radiographic image and the second radiographic image are captured. Therefore, the derived reference line K varies. As a result, in some cases, in the measurement of the bone density of the same subject W, the derived bone density varies even though there is no substantial change in the bone density of the subject W.

In contrast, according to the console 18 of this embodiment, it is possible to derive an appropriate reference line K. Therefore, the value of bone density is stably obtained and the reproducibility of the value of bone density increases.

For example, the configuration and operation of the radiography system 10, the radiography apparatus 16, and the console 18 described in each of the above-mentioned embodiments are illustrative and can be changed according to situations, without departing from the scope and spirit of the invention.

For example, the first embodiment and the second embodiment may be combined with each other.

Figure 24:
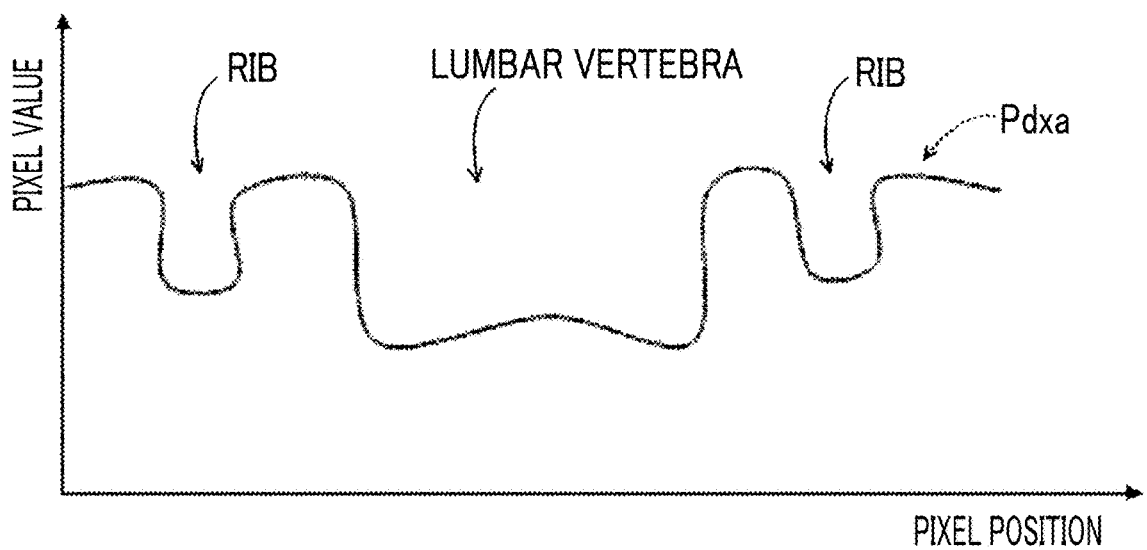
FIG. 24 is a diagram illustrating an example of a profile curve of a DXA profile in a DXA image in a case in which a rib is included.
Figure 25:
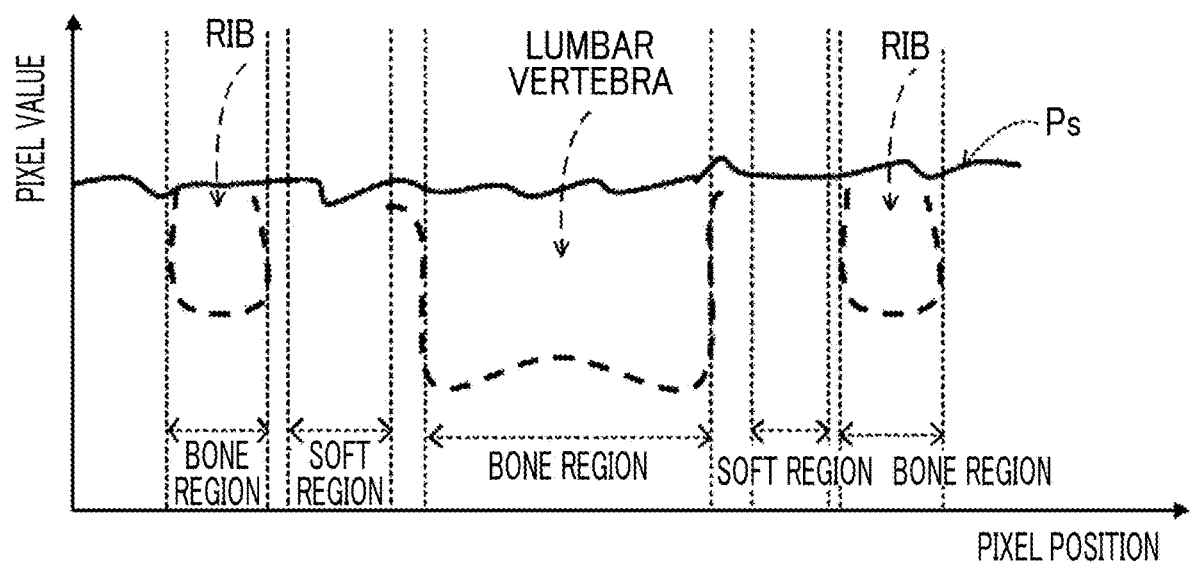
FIG. 25 is a diagram illustrating an example of a soft region specified from a profile curve of a soft part profile in a case in which the rib is included.

For example, in a case in which the initial soft region is used, it is difficult to appropriately derive the reference line K in some imaging parts. A region for deriving the reference line K may be specified by the ES image soft region specification process (see FIG. 13) described in the first embodiment. For example, in a case in which the imaging part is the first lumbar vertebra (a lumbar vertebra closest to the head: L1), a rib is likely to be included in the radiographic image. In this case, as illustrated in FIG. 24, the image of the rib is likely to be included in the profile curve Pdxa of the DXA profile in the DXA image and a region corresponding to the rib is likely to be superimposed on the position of the initial soft region. For this reason, the control unit 80 of the console 18 generates a bone part ES image, using the ES image soft region specification process, derives a bone part profile from the generated bone part ES image, and specifies a bone region using the profile curve Pb of the bone part profile. In addition, the control unit 80 generates a soft part ES image, derives a soft part profile from the generated soft part ES image, and specifies a soft region on the basis of, for example, the profile curve Ps of the soft part profile and the specified bone region as illustrated in FIG. 25. The control unit 80 derives bone density, using the reference line K derived from the specified soft region. Therefore, it is possible to improve the accuracy of derivation of the bone density.

Figure 26:
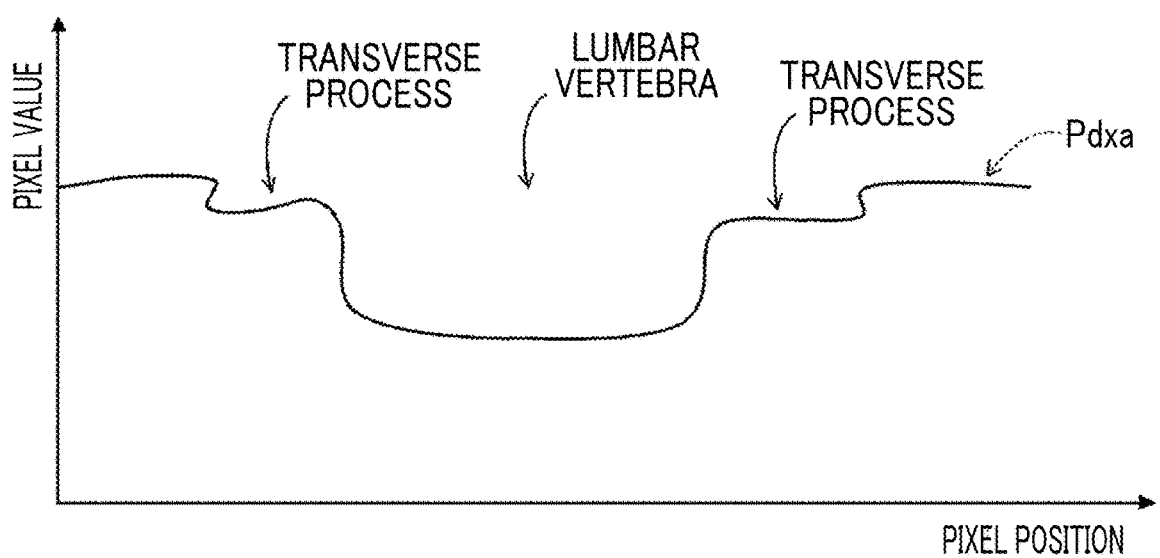
FIG. 26 is a diagram illustrating an example of a profile curve of a DXA profile in a DXA image in a case in which a transverse process is included.
Figure 27:
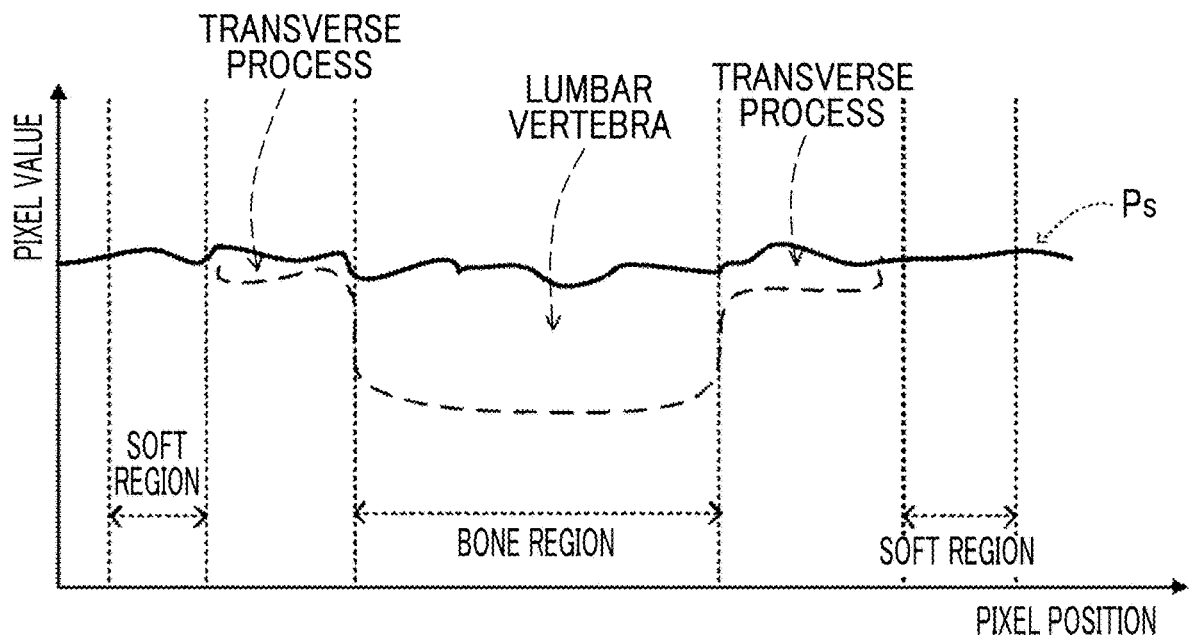
FIG. 27 is a diagram illustrating an example of a soft region specified from a profile curve of a soft part profile in a case in which the transverse process is included.

For example, in a case in which the imaging part is the lumbar vertebra, a transverse process is likely to be included in the radiographic image. In this case, as illustrated in FIG. 26 in which the transverse process is included, the image of the transverse process is likely to be included in the profile curve Pdxa of the DXA profile in the DXA image and a region corresponding to the transverse process is likely to be superimposed on the position of the initial soft region. For this reason, the control unit 80 of the console 18 generates a bone part ES image, using the ES image soft region specification process, derives a bone part profile from the generated bone part ES image, and specifies a bone region using the profile curve Pb of the bone part profile. In addition, the control unit 80 generates a soft part ES image, derives a soft part profile from the generated soft part ES image, and specifies a soft region on the basis of, for example, the profile curve Ps of the soft part profile and the specified bone region as illustrated in FIG. 27. The control unit 80 derives bone density, using the reference line K derived from the specified soft region. Therefore, it is possible to improve the accuracy of derivation of the bone density.

In each of the above-described embodiments, it is determined whether the reference line K is derived from the initial soft region on the basis of whether noise is superimposed, whether the gas region G is present, or whether a component caused by the scattered rays is present. However, the criterion for whether the reference line K is derived from the initial soft region is not limited thereto. For example, whether the reference line K is derived from the initial soft region may be determined on the basis of whether an artifact, such as an implant, is present. In a case in which an artifact is not included, it may be determined that the reference line K is derived from the initial soft region.

For example, evaluation may be performed on the basis of whether an artifact, such as an implant, is present, the size of the irradiation field, or the position of the bone tissue (bone part image). For example, in a case in which an artifact is not included, it is determined that the reference line K is derived from the initial soft region. In a case in which an artifact is included, it is determined that the reference line K is not capable of being derived from the initial soft region. Therefore, a region other than an artifact region including an artifact may be specified as the soft region and the reference line K may be derived from the specified soft region.

In a case in which the backbone is bent, for example, in the case of scoliosis, the bone part image is located outside the vicinity of the center of the image and is close to the outside of the irradiation field. Therefore, as described above, the gap between the bone part image and the outside of the irradiation field is small. For this reason, it is determined whether the reference line K is derived from the initial soft region on the basis of whether the bone tissue is located at a predetermined position. For example, in a case in which the bone tissue (bone image) is located in the vicinity of the center of the image, it is determined that the reference line K is derived from the initial soft region. In the case in which the bone tissue (bone image) is located outside the vicinity of the center of the image, it is determined that the reference line K is not capable of being derived from the initial soft region. Therefore, the reference line K may be derived from the specified soft region.

In addition, it may be determined whether the reference line K is derived from the initial soft region, on the basis of the imaging conditions of the first radiographic image and the second radiographic image. The imaging conditions include, for example, the position of the irradiation field. In a case in which the position of the bone part image in the radiographic image is in the vicinity of the outside of the irradiation field, the gap (distance) from the bone part image to the outside of the irradiation field is small. Therefore, in a case in which the size of the irradiation field is equal to or greater than a predetermined size, it is determined that the reference line K is derived from the initial soft region. In a case in which the size of the irradiation field is less than the predetermined size, it is determined that the reference line K is not capable of being derived from the initial soft region. Therefore, the reference line K may be derived from the specified soft region.

Figure 28:
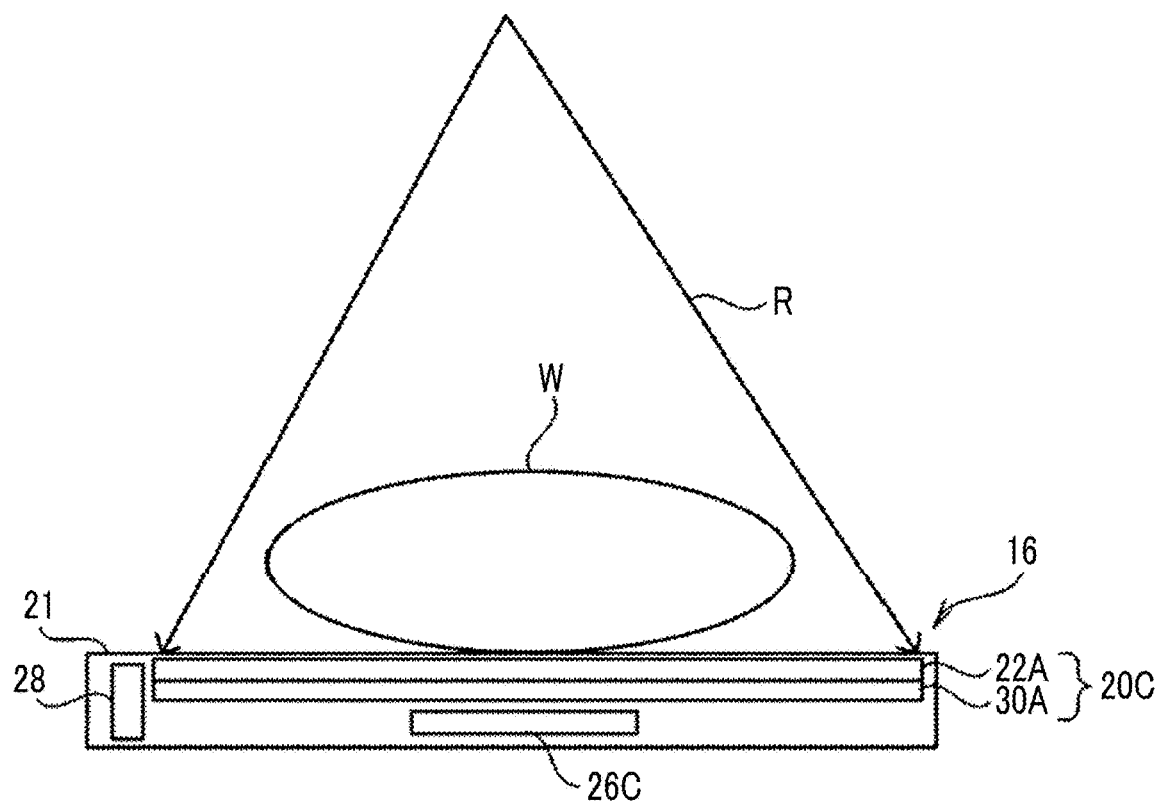
FIG. 28 is a side cross-sectional view illustrating another example of the configuration of the radiography apparatus.

In the above-described embodiments, the radiography apparatus 16 includes two radiation detectors. However, for example, as illustrated in FIG. 28, the radiography apparatus 16 may include a single radiation detector. In the example illustrated in FIG. 28, a radiation detector 20C that detects the radiation R transmitted through the subject W and a control substrate 26C are provided in the housing 21 of the radiography apparatus 16. The configuration of the radiation detector 20C is the same as that of the first radiation detector 20A according to the first embodiment and the configuration of the control substrate 26C is the same as that of the control substrate 26A according to the first embodiment. Therefore, the description thereof will not be repeated here.

In the radiography apparatus 16 illustrated in FIG. 28, two radiography operations are performed at different tube voltages from the radiation emitting apparatus 12 and bone density is derived on the basis of radiographic image data captured by the radiation detector 20C in the two radiography operations. Since different tube voltages are used in the two radiography operations, the radiation detector 20C is irradiated with the radiations R having different energy levels.

Figure 29:
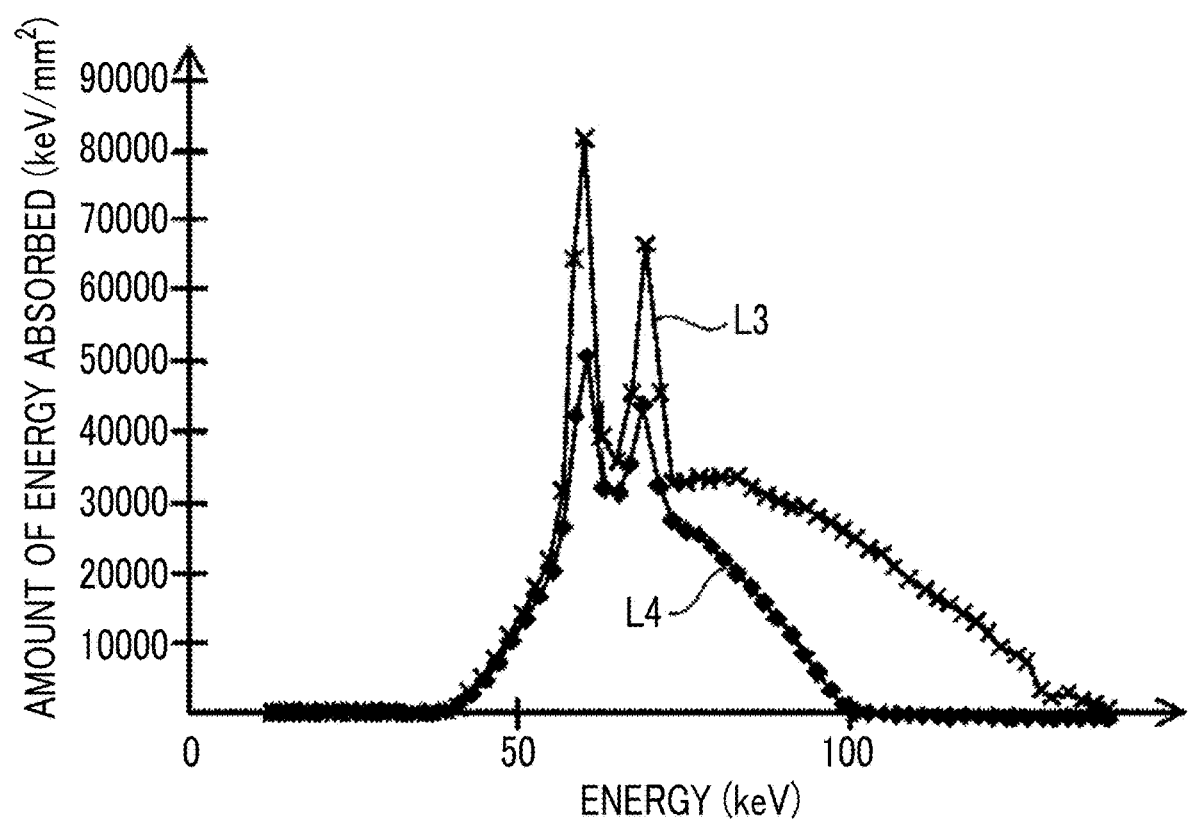
FIG. 29 is a graph illustrating the amount of radiation absorbed by a radiation detector in a case in which radiation is emitted at different tube voltages.

The radiation R absorbed by the radiation detector 20C will be described with reference to FIG. 29. In FIG. 29, the vertical axis indicates the amount of radiation R absorbed per unit area and the horizontal axis indicates the energy of the radiation R. In addition, in FIG. 29, a solid line L3 indicates the relationship between the energy of the radiation R absorbed by the radiation detector 20C and the amount of radiation R absorbed per unit area in a case in which the tube voltage of the radiation source 14 is 140 kV. In FIG. 29, a solid line L4 indicates the relationship between the energy of the radiation R absorbed by the radiation detector 20C and the amount of radiation R absorbed per unit area in a case in which the tube voltage of the radiation source 14 is 100 kV. As illustrated in FIG. 29, since the tube voltages of the radiation source 14 are different from each other, the radiation detector 20C is irradiated with the radiations R having different energy levels in first irradiation and second irradiation.

In each of the above-described embodiments, the image display process performed by the console 18 may be performed by the control unit 58A or the control unit 58B of the radiography apparatus 16. In addition, in a case in which the radiography apparatus 16 includes an overall control unit that controls the overall operation of the control unit 58A and the control unit 58B, the overall control unit may perform the bone density derivation process or the image display process. Furthermore, for example, an image processing apparatus that is connected to the console 18 through the network may perform the image display process.

In the first embodiment, the case in which an indirect-conversion-type radiation detector that converts radiation into light and converts the converted light into charge is applied to both the first radiation detector 20A and the second radiation detector 20B has been described. However, the invention is not limited thereto. For example, a direct-conversion-type radiation detector that directly converts radiation into charge may be applied to at least one of the first radiation detector 20A or the second radiation detector 20B. In addition, for example, a conversion layer that absorbs radiation and converts the radiation into charge in the direct-conversion-type radiation detector is made of amorphous selenium (a-Se) and crystalline cadmium telluride (CdTe).

In the first embodiment, the case in which the irradiation side sampling radiation detectors in which the radiation R is incident from the TFT substrates 30A and 30B are applied to the first radiation detector 20A and the second radiation detector 20B, respectively, has been described. However, the invention is not limited thereto. For example, a so-called penetration side sampling (PSS) radiation detector in which the radiation R is incident from the scintillator 22A or 22B may be applied to at least one of the first radiation detector 20A or the second radiation detector 20B.

In each of the above-described embodiments, the case in which bone density is derived using the first radiographic image data and the second radiographic image data has been described. However, the invention is not limited thereto. For example, bone mineral content or both bone density and bone mineral content may be derived using the first radiographic image data and the second radiographic image data. In a case in which bone mineral content is derived, bone density is derived using the profile curve Pdxa of the DXA profile derived from the DXA image, similarly to the derivation of the bone density. Therefore, the same task as that in the case in which the bone density is derived occurs. As a result, for example, the same effect as that in each of the above-described embodiments is obtained in a case in which the bone mineral content is derived instead of the bone density in each of the above-described embodiments.

In each of the above-described embodiments, the image processing performed by the execution of software (program) by the CPU 82 of the control unit 80 may be performed by various processors other than the CPU 82. In this case, examples of the processor include a programmable logic device (PLD) whose circuit configuration can be changed after manufacture, such as a field-programmable gate array (FPGA), and a dedicated electric circuit, such as an application specific integrated circuit (ASIC), which is a processor having a dedicated circuit configuration designed to perform a specific process. In addition, the image processing may be performed by one of the various processors or may be performed by a combination of two or more processors of the same type or different types (for example, a combination of a plurality of FPGAs and a combination of a CPU and an FPGA). Specifically, the hardware structure of the various processors is an electric circuit obtained by combining circuit elements such as semiconductor elements.

In each of the above-described embodiments, the aspect in which the image processing program is stored (installed) in the ROM 84 in advance has been described. However, the invention is not limited thereto. The image processing program may be recorded on a recording medium, such as a compact disk read only memory (CD-ROM), a digital versatile disk read only memory (DVD-ROM), or a universal serial bus (USB) memory, and then provided. In addition, the image processing program may be downloaded from an external apparatus through the network.

What is claimed is:

1. An image processing apparatus comprising:
an acquisition unit, which is a processor, that acquires a first radiographic image generated by a first radiation detector irradiated with radiation with a first energy level and a second radiographic image generated by a second radiation detector irradiated with radiation with a second energy level different from the first energy level from a radiography apparatus including the first and second radiation detectors in which a plurality of pixels, each of which includes a conversion element that generates a larger amount of charge as it is irradiated with a larger amount of radiation, are arranged and which are arranged in a direction in which the radiation is emitted;
a derivation unit, which is a processor, that derives a reference line which satisfies a predetermined accuracy for defining a bone mass, on the basis of a pixel value of a predetermined region corresponding to a soft tissue in a profile indicating a correspondence relationship between a pixel position and the pixel value in a derivation region including a region corresponding to the soft tissue and a region corresponding to a bone tissue in a difference image for derivation which is a difference image between the first radiographic image and the second radiographic image and is used to derive at least one of bone density or bone mineral content; and
a bone derivation unit, which is a processor, that derives at least one of the bone mineral content or the bone density on the basis of a bone mass which is defined on the basis of the reference line in the region corresponding to the bone tissue.

2. An image processing apparatus comprising:
an acquisition unit, which is a processor, that acquires a first radiographic image generated by a single radiation detector irradiated with radiation with a first energy level and a second radiographic image generated by the radiation detector irradiated with radiation with a second energy level different from the first energy level from a radiography apparatus including the radiation detector in which a plurality of pixels, each of which includes a conversion element that generates a larger amount of charge as it is irradiated with a larger amount of radiation, are arranged; and
a derivation unit, which is a processor, that derives a reference line which satisfies a predetermined accuracy for defining a bone mass, on the basis of a pixel value of a predetermined region corresponding to a soft tissue in a profile indicating a correspondence relationship between a pixel position and the pixel value in a derivation region including a region corresponding to the soft tissue and a region corresponding to a bone tissue in a difference image for derivation which is a difference image between the first radiographic image and the second radiographic image and is used to derive at least one of bone density or bone mineral content; and
a bone derivation unit that derives at least one of the bone mineral content or the bone density on the basis of a bone mass which is defined on the basis of the reference line in the region corresponding to the bone tissue.

3. The image processing apparatus according to claim 1, wherein the derivation unit comprises a determination unit, which is a processor, that determines whether the reference line satisfying the predetermined accuracy is capable of being derived, and
in a case in which the determination unit determines that the reference line is capable of being derived, the derivation unit derives the reference line.

4. The image processing apparatus according to claim 3, wherein, in a case in which the determination unit determines that the reference line is not capable of being derived, the derivation unit specifies a region corresponding to the soft tissue and derives the reference line on the basis of a pixel value of the specified region corresponding to the soft tissue.

5. The image processing apparatus according to claim 3, wherein the determination unit determines whether the reference line satisfying the predetermined accuracy is capable of being derived, on the basis of a variation in the pixel value of the region corresponding to the soft tissue in the profile.

6. The image processing apparatus according to claim 5, wherein, in a case in which the determination unit determines that the reference line satisfying the predetermined accuracy is not capable of being derived, the derivation unit derives the reference line on the basis of a pixel value of a region corresponding to the soft tissue which is wider than the predetermined region corresponding to the soft tissue.

7. The image processing apparatus according to claim 3, wherein, in a case in which the profile includes a gas region caused by gas generated in a body of a subject from which at least one of the bone density or the bone mineral content is to be derived, the determination unit determines that the reference line satisfying the predetermined accuracy is not capable of being derived, and the derivation unit derives the reference line on the basis of a pixel value of a region corresponding to the soft tissue between the gas region and the region corresponding to the bone tissue.

8. The image processing apparatus according to claim 3, wherein, in a case in which the profile includes an artifact region caused by an artifact in a body of a subject from which at least one of the bone density or the bone mineral content is to be derived, the determination unit determines that the reference line satisfying the predetermined accuracy is not capable of being derived.

9. The image processing apparatus according to claim 3, wherein, in a case in which a position of a bone tissue used to derive at least one of the bone density or the bone mineral content is different from a predetermined position, the determination unit determines that the reference line satisfying the predetermined accuracy is not capable of being derived.

10. The image processing apparatus according to claim 3, wherein the determination unit determines whether the reference line is capable of being derived on the basis of a condition in which imaging conditions for generating the first radiographic image and the second radiographic image are predetermined.

11. The image processing apparatus according to claim 3, wherein the determination unit determines whether the reference line satisfying the predetermined accuracy is capable of being derived on the basis of an inclination of the entire region corresponding to the soft tissue in the profile.

12. The image processing apparatus according to claim 3, wherein the determination unit determines whether the reference line satisfying the predetermined accuracy is capable of being derived on the basis of whether a component caused by a scattered ray of the radiation is included in the pixel value of the region corresponding to the soft tissue in the profile.

13. The image processing apparatus according to claim 12, wherein, in a case in which the determination unit determines that the reference line satisfying the predetermined accuracy is not capable of being derived, the derivation unit removes the component caused by the scattered ray of the radiation from the pixel value of the predetermined region corresponding to the soft tissue on the basis of a predetermined scattered ray distribution model and derives the reference line.

14. The image processing apparatus according to claim 3, wherein, in a case in which the determination unit determines that the reference line satisfying the predetermined accuracy is not capable of being derived, the derivation unit derives the reference line, on the basis of a pixel value of a region corresponding to the soft tissue which is specified on the basis of at least one of a bone part difference image which is a difference image between the first radiographic image and the second radiographic image and in which the bone tissue is highlighted or a soft part difference image which is a difference image between the first radiographic image and the second radiographic image and in which the soft tissue is highlighted.

15. The image processing apparatus according to claim 1, wherein each of the first and second radiation detectors comprises a light emitting layer that is irradiated with the radiation and emits light,
the plurality of pixels of each of the first and second radiation detectors receive the light, generate the charge, and accumulate the charge, and
the light emitting layer of one of the first and second radiation detectors which is provided on an incident side of the radiation includes CsI and the light emitting layer of the other radiation detector includes GOS.

16. A radiography system comprising:
the image processing apparatus according to claim 1; and
a radiography apparatus that outputs a first radiographic image and a second radiographic image to the image processing apparatus.

17. An image processing method comprising:
acquiring a first radiographic image generated by a first radiation detector irradiated with radiation with a first energy level and a second radiographic image generated by a second radiation detector irradiated with radiation with a second energy level different from the first energy level from a radiography apparatus including the first and second radiation detectors in which a plurality of pixels, each of which includes a conversion element that generates a larger amount of charge as it is irradiated with a larger amount of radiation, are arranged and which are arranged in a direction in which the radiation is emitted;
deriving a reference line which satisfies a predetermined accuracy for defining a bone mass, on the basis of a pixel value of a predetermined region corresponding to a soft tissue in a profile indicating a correspondence relationship between a pixel position and the pixel value in a derivation region including a region corresponding to the soft tissue and a region corresponding to a bone tissue in a difference image for derivation which is a difference image between the first radiographic image and the second radiographic image and is used to derive at least one of bone density or bone mineral content; and
deriving, using a bone derivation unit, which is a processor, at least one of the bone mineral content or the bone density on the basis of a bone mass which is defined on the basis of the reference line in the region corresponding to the bone tissue.

18. An image processing method comprising:
acquiring a first radiographic image generated by a single radiation detector irradiated with radiation with a first energy level and a second radiographic image generated by the radiation detector irradiated with radiation with a second energy level different from the first energy level from a radiography apparatus including the radiation detector in which a plurality of pixels, each of which includes a conversion element that generates a larger amount of charge as it is irradiated with a larger amount of radiation, are arranged;

deriving a reference line which satisfies a predetermined accuracy for defining a bone mass, on the basis of a pixel value of a predetermined region corresponding to a soft tissue in a profile indicating a correspondence relationship between a pixel position and the pixel value in a derivation region including a region corresponding to the soft tissue and a region corresponding to a bone tissue in a difference image for derivation which is a difference image between the first radiographic image and the second radiographic image and is used to derive at least one of bone density or bone mineral content; and deriving, using a bone derivation unit, which is a processor, at least one of the bone mineral content or the bone density on the basis of a bone mass which is defined on the basis of the reference line in the region corresponding to the bone tissue.

\* \* \* \* \*